US011452810B2

(12) United States Patent
Robinson et al.

(10) Patent No.: US 11,452,810 B2

(45) Date of Patent: Sep. 27, 2022

(54) APPARATUS, SYSTEM, AND METHOD FOR MECHANICAL INDICATION OF PRESSURE

(71) Applicant: KCI LICENSING, INC., San Antonio, TX (US)

(72) Inventors: Timothy Mark Robinson, Wimbourne (GB); Christopher Brian Locke, Bournemouth (GB)

(73) Assignee: KCI Licensing, Inc., San Antonio, TX (US)

(*) Notice: Subject to any disclaimer, the term of this patent is extended or adjusted under 35 U.S.C. 154(b) by 0 days.

(21) Appl. No.: 17/292,917

(22) PCT Filed: Nov. 11, 2019

(86) PCT No.: PCT/US2019/060674

§ 371 (c)(1), (2) Date: May 11, 2021

(87) PCT Pub. No.: WO2020/102049

PCT Pub. Date: May 22, 2020

(65) Prior Publication Data

US 2022/0016331 A1 Jan. 20, 2022

Related U.S. Application Data

(60) Provisional application No. 62/767,321, filed on Nov. 14, 2018.

(51) Int. Cl.

*A61M 1/00* (2006.01)

(52) U.S. Cl.

CPC ..... *A61M 1/912* (2021.05); *A61M 2205/0216* (2013.01); *A61M 2205/183* (2013.01);

(Continued)

(58) Field of Classification Search

CPC .......... A61M 1/912; A61M 2205/0216; A61M 2205/183; A61M 2205/3341;

(Continued)

(56) References Cited

U.S. PATENT DOCUMENTS 1,355,846 A 10/1920 Rannells
2,547,758 A 4/1951 Keeling (Continued)

FOREIGN PATENT DOCUMENTS

AU 550575 B2 3/1986
AU 745271 B2 3/2002

(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

(Continued)

*Primary Examiner* — Susan S Su
*Assistant Examiner* — Eric Rassavong

(57) ABSTRACT

This disclosure describes devices, systems, and methods related to a connector for a dressing, such as a dressing of a hyperbaric oxygen therapy system. An example of a connector includes a connector body configured to define at least a portion of a first channel. The connector also includes a viewing member coupled to the connector body. The connector further includes a deformable member positioned within the first channel. The deformable member is configured to deform based on a pressure associated with the deformable member and to provide a visual indication, via the viewing member, of the pressure.

18 Claims, 8 Drawing Sheets

230 300 248 272 246 262 332 256 350A 264 242 252 254 350B 250 244 350B 247 320

(52) U.S. Cl.
CPC ............... *A61M 2205/3341* (2013.01); *A61M 2205/3344* (2013.01); *A61M 2205/581* (2013.01); *A61M 2205/584* (2013.01)

(58) Field of Classification Search
CPC .. A61M 2205/584; A61M 1/732; A61M 1/90; A61F 13/00068
See application file for complete search history.

(56) References Cited

U.S. PATENT DOCUMENTS 2,632,443 A 3/1953 Lesher
2,682,873 A 7/1954 Evans et al.
2,910,763 A 11/1959 Lauterbach
2,969,057 A 1/1961 Simmons
3,066,672 A 12/1962 Crosby, Jr. et al.
3,367,332 A 2/1968 Groves
3,520,300 A 7/1970 Flower, Jr.
3,568,675 A 3/1971 Harvey
3,648,692 A 3/1972 Wheeler
3,682,180 A 8/1972 McFarlane
3,826,254 A 7/1974 Mellor
4,080,970 A 3/1978 Miller
4,096,853 A 6/1978 Weigand
4,139,004 A 2/1979 Gonzalez, Jr.
4,165,748 A 8/1979 Johnson
4,184,510 A 1/1980 Murry et al.
4,233,969 A 11/1980 Lock et al.
4,245,630 A 1/1981 Lloyd et al.
4,256,109 A 3/1981 Nichols
4,261,363 A 4/1981 Russo
4,275,721 A 6/1981 Olson
4,284,079 A 8/1981 Adair
4,297,995 A 11/1981 Golub
4,333,468 A 6/1982 Geist
4,373,519 A 2/1983 Errede et al.
4,382,441 A 5/1983 Svedman
4,392,853 A 7/1983 Muto
4,392,858 A 7/1983 George et al.
4,419,097 A 12/1983 Rowland
4,465,485 A 8/1984 Kashmer et al.
4,475,909 A 10/1984 Eisenberg
4,480,638 A 11/1984 Schmid
4,525,166 A 6/1985 Leclerc
4,525,374 A 6/1985 Vaillancourt
4,540,412 A 9/1985 Van Overloop
4,543,100 A 9/1985 Brodsky
4,548,202 A 10/1985 Duncan
4,551,139 A 11/1985 Plaas et al.
4,569,348 A 2/1986 Hasslinger
4,605,399 A 8/1986 Weston et al.
4,608,041 A 8/1986 Nielsen
4,640,688 A 2/1987 Hauser
4,655,754 A 4/1987 Richmond et al.
4,664,662 A 5/1987 Webster
4,710,165 A 12/1987 McNeil et al.
4,733,659 A 3/1988 Edenbaum et al.
4,743,232 A 5/1988 Kruger
4,758,220 A 7/1988 Sundblom et al.
4,787,888 A 11/1988 Fox
4,826,494 A 5/1989 Richmond et al.
4,838,883 A 6/1989 Matsuura
4,840,187 A 6/1989 Brazier
4,863,449 A 9/1989 Therriault et al.
4,872,450 A 10/1989 Bustad
4,878,901 A 11/1989 Sachse
4,897,081 A 1/1990 Poirier et al.
4,906,233 A 3/1990 Moriuchi et al.
4,906,240 A 3/1990 Reed et al.
4,919,654 A 4/1990 Kalt
4,941,882 A 7/1990 Ward et al.
4,953,565 A 9/1990 Tachibana et al.
4,969,880 A 11/1990 Zamierowski
4,985,019 A 1/1991 Michelson
5,037,397 A 8/1991 Kalt et al.
5,086,170 A 2/1992 Luheshi et al.
5,092,858 A 3/1992 Benson et al.
5,100,396 A 3/1992 Zamierowski
5,134,994 A 8/1992 Say
5,149,331 A 9/1992 Ferdman et al.
5,167,613 A 12/1992 Karami et al.
5,176,663 A 1/1993 Svedman et al.
5,215,522 A 6/1993 Page et al.
5,232,453 A 8/1993 Plass et al.
5,261,893 A 11/1993 Zamierowski
5,278,100 A 1/1994 Doan et al.
5,279,550 A 1/1994 Habib et al.
5,298,015 A 3/1994 Komatsuzaki et al.
5,342,376 A 8/1994 Ruff
5,344,415 A 9/1994 DeBusk et al.
5,358,494 A 10/1994 Svedman
5,437,622 A 8/1995 Carion
5,437,651 A 8/1995 Todd et al.
5,527,293 A 6/1996 Zamierowski
5,549,584 A 8/1996 Gross
5,556,375 A 9/1996 Ewall
5,607,388 A 3/1997 Ewall
5,636,643 A 6/1997 Argenta et al.
5,645,081 A 7/1997 Argenta et al.
6,071,267 A 6/2000 Zamierowski
6,135,116 A 10/2000 Vogel et al.
6,241,747 B1 6/2001 Ruff
6,287,316 B1 9/2001 Agarwal et al.
6,345,623 B1 2/2002 Heaton et al.
6,488,643 B1 12/2002 Tumey et al.
6,493,568 B1 12/2002 Bell et al.
6,553,998 B2 4/2003 Heaton et al.
6,814,079 B2 11/2004 Heaton et al.
8,529,526 B2 9/2013 Wilkes et al.
8,690,845 B2 * 4/2014 Long ...................... A61M 1/90 604/319
2002/0077661 A1 6/2002 Saadat
2002/0115951 A1 8/2002 Norstrem et al.
2002/0120185 A1 8/2002 Johnson
2002/0143286 A1 10/2002 Tumey
2010/0160901 A1 6/2010 Hu et al.
2011/0224633 A1 * 9/2011 Robinson ................ A61M 1/90 604/319
2015/0073361 A1 3/2015 Pratt et al.
2018/0154052 A1 * 6/2018 Chien .................. A61M 1/732

FOREIGN PATENT DOCUMENTS

AU 755496 B2 12/2002
CA 2005436 A1 6/1990
CN 107929833 A 4/2018
DE 26 40 413 A1 3/1978
DE 43 06 478 A1 9/1994
DE 29 504 378 U1 9/1995
EP 0100148 A1 2/1984
EP 0117632 A2 9/1984
EP 0161865 A2 11/1985
EP 0358302 A2 3/1990
EP 1018967 A1 7/2000
GB 692578 A 6/1953
GB 2 195 255 A 4/1988
GB 2 197 789 A 6/1988
GB 2 220 357 A 1/1990
GB 2 235 877 A 3/1991
GB 2 329 127 A 3/1999
GB 2 333 965 A 8/1999
GB 2 511 523 A 9/2014
JP 4129536 B2 8/2008
SG 71559 4/2002
WO 80/02182 A1 10/1980
WO 87/04626 A1 8/1987
WO 90/010424 A1 9/1990
WO 93/009727 A1 5/1993
WO 94/020041 A1 9/1994
WO 96/05873 A1 2/1996
WO 97/18007 A1 5/1997

(56) References Cited

FOREIGN PATENT DOCUMENTS

| | | | |
|---|---|---|---|
| WO | 99/13793 | A1 | 3/1999 |
| WO | WO-2018/192978 | A1 | 10/2018 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al.; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al.; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., JR., et al.; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al.; "Vacuum Treatment in the Surgical Management of Purulent Wounds"; Vestnik Khirurgi, Sep. 1986, pp. 18-21 and 6 page English translation thereof.
Davydov, Yu. A., et al.; "Vacuum Therapy in the Treatment of Purulent Lactation Mastitis"; Vestnik Khirurgi, May 14, 1986, pp. 66-70, and 9 page English translation thereof.
Yusupov. Yu.N., et al.; "Active Wound Drainage", Vestnki Khirurgi, vol. 138, Issue 4, 1987, and 7 page English translation thereof.
Davydov, Yu.A., et al.; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al.; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Septembers, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax, " Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.
International Search Report and Written Opinion for International Patent Application No. PCT/US2019/060674 dated Feb. 10, 2020 (12 pages).

* cited by examiner

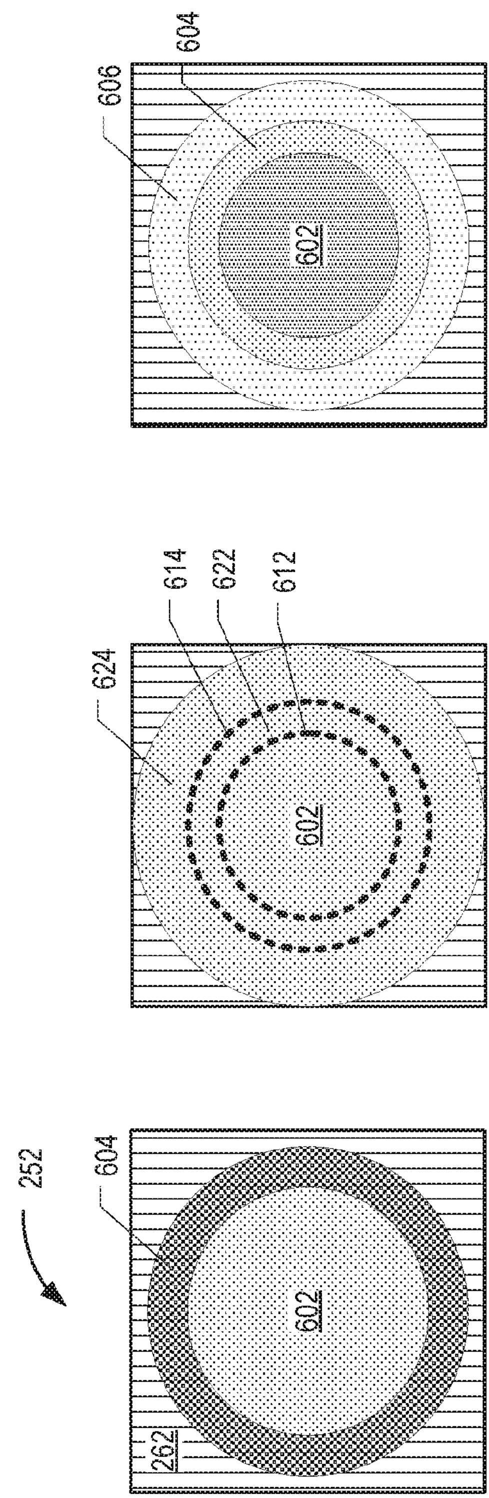
FIG. 6C
FIG. 6B
FIG. 6A
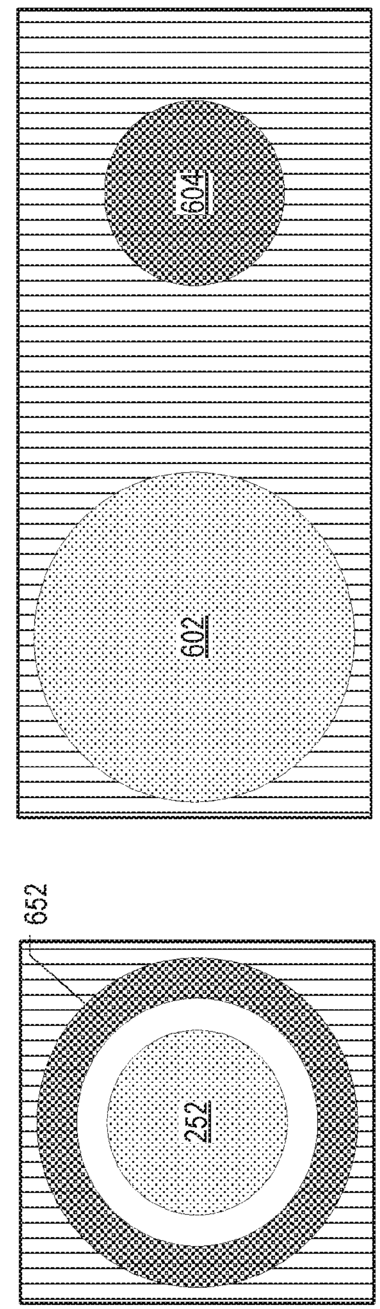
FIG. 6E
FIG. 6D

APPARATUS, SYSTEM, AND METHOD FOR MECHANICAL INDICATION OF PRESSURE

CROSS-REFERENCE TO RELATED APPLICATIONS

The present application is a US national phase application under 35 USC § 371 of International Application No. PCT/US2019/060674, filed on Nov. 11, 2019, which claims the benefit, under 35 USC 119(e), of U.S. Provisional Patent Application No. 62/767,321, entitled "Apparatus, System, and Method For Mechanical Indication of Pressure" filed Nov. 14, 2018, the contents of each of which are hereby incorporated into the present application in their entireties.

TECHNICAL FIELD

Aspects of the present disclosure relate generally to a mechanical pressure indicator, and more specifically, but not by way of limitation, to a mechanical pressure indicator for a dressing and/or a system for oxygen therapy and related methods.

BACKGROUND

Clinical studies and practice have shown that oxygen therapy in proximity to a tissue site can augment and accelerate growth of new tissue at the tissue site. Applications of this phenomenon are numerous, but have proven particularly advantageous for treating wounds. Regardless of the etiology of a wound, whether trauma, surgery, or another cause, care of the wound can impact the outcome. Treatment of wounds with oxygen therapy may be commonly referred to as "hyperbaric oxygen wound therapy," but is also known by other names, including "hyperbaric oxygen therapy," "positive-pressure therapy," "positive pressure wound therapy," and "hyperbaric therapy," as illustrative, non-limiting examples. Oxygen therapy may provide one or more benefits, including migration of epithelial and subcutaneous tissues, improved blood flow, reduced infection, and/or micro-deformation of tissue at a wound site. These benefits can increase development of granulation tissue and reduce healing times.

Oxygen therapy is typically provided by a positive-pressure system (e.g., a pressurized system or a hyperbaric system) including one or more components and/or one or more devices. To illustrate, a conventional positive-pressure system may include a dressing, one or more tubes, a therapy device (e.g., a positive-pressure source), or a combination thereof, as illustrative, non-limiting examples. The dressing may be placed at a tissue site and coupled to the positive-pressure source via the tube. The positive-pressure source is configured to establish positive-pressure (e.g., a hyperbaric environment) at the dressing and the dressing is configured to maintain the positive-pressure at the tissue site.

However, excess positive-pressure at the dressing and tissue site can restrict or close capillaries, which reduces blood flow and increases healing times. Additionally, a user may be unaware of such a situation and damage can occur. To address excess positive-pressure (e.g., an overpressure condition), dressings and/or therapy systems have specific and/or dedicated electronic monitoring, sensors, etc., to regulate the pressure at the tissue site. Additionally, dressings and/or therapy systems may include back-up systems and/or safety measures, such as automatic shut off and/or alarms to notify a user. To illustrate, a dressing may include expensive regulators and electronic components to facilitate pressure monitoring and/or regulation at the dressing and tissue site. These components add size, weight, and rigidity to the dressing, which decreases efficacy and patient comfort.

SUMMARY

This disclosure describes devices, systems, and methods related to a pressure indicator, such as a mechanical indicator, coupled to a connector for a dressing. The connector and/or the dressing may be associated with a hyperbaric oxygen therapy system, that includes pressure indication by a mechanical indicator. The dressing is configured to be coupled to a tissue site and, when coupled to the tissue site, defines a cavity to which pressure-pressure is applied to create a pressurized, oxygen-rich environment (e.g., an environment having a higher concentration of oxygen that atmospheric or ambient air). The connector coupled to dressing includes a connector body (e.g., a housing) configured to define at least a portion of a first channel. The connector further includes a viewing member (e.g., a window) coupled to the connector body and a deformable member (e.g., a deformable indicator) positioned within the first channel and viewable through the viewing member.

The deformable member is configured to deform responsive to positive-pressure associated with the tissue site to provide one or more visual indications of pressure. For example, the deformable member deforms under increasing positive-pressure to move or expand towards the viewing member to provide a particular visual indication of pressure. As an illustrative, non-limiting example, when exposed to a first pressure above a threshold pressure, the deformable member deforms such that a portion of the deformable member contacts a portion of the viewing member. The portion of the deformable member in contact with the viewing member may be clearly visible through the viewing member. When exposed to a second pressure below the threshold pressure, the deformable member may not deform (or may deform to a lesser extent as compared to when exposed to the first pressure above the threshold pressure) such that at least a portion of the deformable member is partially occluded the viewing member (e.g., not clearly visible through the viewing member). Thus, a user (e.g., a patient or care provider) can determine a pressure state or an operational state of the dressing/connector based on the visual indication of the deformable member.

To illustrate, when the deformable member does not provide a particular visual indication (e.g., is not visible via the viewing member or is partially occluded by the viewing member), the deformable member may provide a first indication, such as the dressing connector is in a non-operational or neutral-pressure state. That is, a lack of a visual indication can still provide an indication of pressure or status to the patient or care provider. When the deformable member provides a particular visual indication (e.g., is visible via the viewing member), the deformable member provides a second indication, such as the dressing/connector is in an operational or positive-pressure state, or an overpressure state.

In some implementations in which the second indication corresponds to the dressing/connector in an operational or positive-pressure state, the connector body is configured to provide a second visual indication (e.g., a third indication). For example, the connector body includes a second deformable indicator configured to deform responsive to another pressure threshold to provide the second visual indication which indicates excess positive-pressure or an overpressure state. When the deformable member is exposed to the higher pressure and is deformed to a greater extent, an additional portion of the deformable member is visible via the viewing member. In a particular implementation, the additional portion of the deformable member has a different color or marking from first portion of the deformable member visible via the viewing member when the deformable member is exposed to an operational positive-pressure, such as a pressure greater than or equal to the pressure threshold (e.g., a first pressure threshold), and less than or equal to the other pressure threshold (e.g., a second pressure threshold).

In some implementations, the connector further includes a pressure relief valve. The pressure relief valve may be positioned within a second channel (or integrated into the connector body) defined by the connector body and configured to enable flow based on the pressure associated with a tissue site. For example, the pressure relief valve may move or deform to create an opening in the second channel, thereby enabling pressure in the first cavity to be released via the second channel.

Thus, the connector (e.g., the deformable member) of the present disclosure is configured to enable mechanical pressure indication. For example, the deformable member provides a visual indication of a pressure range and is configured to respond to different pressures by deforming to provide a corresponding visual indication. To illustrate, when the connector is coupled to a positive-pressure source (e.g., a pressurized oxygen source) such that positive-pressure (e.g., pressurized oxygen) is provided to the cavity associated with a tissue site, the deformable member deforms to indicate that a pressure associated with the tissue site is at a particular pressure or within a range. The range indicated by the deformable member may correspond to a range of pressures associated with hyperbaric therapy and thus, the deformable member indicates that hyperbaric therapy is being applied to the tissue site. Therefore, a patient or care provider can determine a pressure and/or operational statues of the dressing and/or therapy applied to the tissue site and adjust or regulate the pressure accordingly.

Additionally, the connector of the present disclosure may be configured to enable mechanical pressure regulation. For example, the pressure relief valve is configured to enable flow based on the pressure of cavity and tissue site when the pressure is greater than equal to a threshold value. To illustrate, when the connector is coupled to the positive-pressure source such that excess positive-pressure is provided to the cavity, the pressure relief valve deforms to vent excess pressure and reduce or limit an amount of positive-pressure applied to the tissue site. Reducing/limiting the amount of positive-pressure at the tissue site enables the connector to advantageously avoid excess positive-pressure at the tissue site when the connector is coupled to a positive-pressure source, such as an unregulated pressure source. Additionally, the connector beneficially provides an ability to reduce and/or limit the delivery of positive-pressure to the tissue site such that capillaries of the tissue site remain open. Accordingly, effective, efficient, and safe positive-pressure therapy may be achieved through use of the flexible mechanical indicators and regulators, thereby advancing connector flexibility and patient comfort and confidence in the treatment.

Some embodiments of the present apparatuses (e.g., of a connector) comprise: a connector body configured to define at least a portion of a first channel; a viewing member coupled to the connector body; and a deformable member positioned within the first channel and configured to deform based on a pressure of a cavity partially defined by the deformable member and to provide a visual indication, via the viewing member, of the pressure of the cavity. In some implementations of the embodiments of the present apparatuses, the deformable member is configured to provide a first visual indication, via the viewing member, when the pressure of the cavity is greater than or equal to a first threshold. In a particular implementation, the deformable member comprises an elastic polymer. Additionally, or alternatively, in one or more implementations, the deformable member has a hardness in the range of 10 Shore A to 20 Shore A.

In some of the foregoing embodiments of the present apparatuses, the cavity is distinct from a second cavity defined by the connector body, the viewing member.

Additionally, or alternatively, the deformable member, and the deformable member is configured to deform responsive to a force resulting from a pressure differential between the cavity and the second cavity.

In some of the foregoing embodiments of the present apparatuses, the deformable member is configured to deform to transition between a first state and a second state; when the deformable member is in the first state, the deformable member is configured to indicate a neutral pressure state; and/or when the deformable member is in the second state, at least a portion of the deformable member is viewable through the viewing member and configured to indicate a positive-pressure state. In some such implementations, the first state comprises an undeformed state, and the second state comprises a deformed state. Additionally, or alternatively, when the deformable member is in the first state, the deformable member does not contact the viewing member; and/or when the deformable member is in the second state, at least a first portion of the deformable member contacts the viewing member. In a particular implementation, the first portion has a first color or marking.

In some of the foregoing embodiments of the present apparatuses, the deformable member is configured to provide a second visual indication, via the viewing member, when the pressure of the cavity is greater than or equal to a second threshold. Additionally, or alternatively, the deformable member is configured to deform to transition between the second state and a third state. In some such implementations, when the deformable member is in the third state, at least a second portion of the deformable member contacts the viewing member; the second portion has a second color or marking that is different from the first color or marking of the first portion; and/or and the first state corresponds to a first range of pressures, the second state corresponds to a second range of pressures, and the third state corresponds to a third range of pressures. In a particular implementation, the second visual indication indicates an over-pressure state. Additionally, or alternatively, is one or more implementations, the deformable member is configured to transition to the second state between 10 mm Hg and 22 mm Hg.

In some of the foregoing embodiments of the present apparatuses, the apparatuses (e.g., the connector) further comprises a pressure relief valve positioned within a second channel defined by the connector body and configured to enable flow when the pressure of the cavity is greater than equal to a threshold value. In some such implementations, the pressure relief valve includes a valve selected from the group consisting of: a duckbill valve, an umbrella valve, and a combination duckbill umbrella valve; and, optionally, the pressure relief valve has a hardness in the range of 40 Shore A to 60 Shore A. In a particular implementations, the threshold value associated with the pressure relief valve is between 22 mm Hg and 35 mm Hg. Additionally, or alternatively, the pressure relief valve may be configured to generate an audio indication responsive to flow through the pressure relief valve.

In some of the foregoing embodiments of the present apparatuses, the viewing member comprises a window. In some such implementations, the window comprises a transparent material or a translucent material such that the deformable member is at least partially occluded by the window in when the deformable member is in the first state and is visible via the window when the deformable member is in a second state. In a particular implementation, the window comprises frosted glass and is semi-opaque. In some of the foregoing embodiments of the present apparatuses, the deformable member comprises a first material that is different from a second material of the viewing member such that the first material does not adhere to the second material when the deformable member contacts the viewing member.

In some of the foregoing embodiments of the present apparatuses, the apparatuses (e.g., the connector) further comprises a hydrophobic filter configured to prevent liquid from flowing from the cavity to the pressure relief valve. Additionally, or alternatively, the apparatuses (e.g., the connector) further comprises a second deformable member configured to deform to indicate an over pressurized state. In some such implementations, the apparatuses (e.g., the connector) further comprises a second viewing member, where the second deformable member is positioned in the first channel and visible via the second viewing member. In a particular implementation, the deformable member and the second deformable member are integrated into a deformable indicator, and the deformable member comprises a first portion of the deformable indicator and the second deformable member comprises a second portion of the deformable indicator In some of the foregoing embodiments of the present apparatuses, the connector is configured to be coupled to a positive-pressure dressing. In some such implementations, the apparatuses (e.g., the connector) further comprises a second deformable member configured to deform to indicate a reduced-pressure state.

Some embodiments of the present apparatuses (e.g., of a dressing) comprise: a connector the comprises: a connector body configured to define at least a portion of a first channel; a viewing member coupled to the connector body; and a deformable member positioned within the first channel and configured to deform based on a pressure of a cavity partially defined by the deformable member and to provide a visual indication, via the viewing member, of the pressure of the cavity; and a drape coupled to the connector and configured to be coupled to a tissue site. In some implementations of the embodiments of the present apparatuses, the dressing further comprises a tube configured to be coupled to the connector and comprising one or more lumens. In some such implementations, the tube is coupled to a port of the connector, and/or the tube comprises multiple lumens including a primary lumen, one or more ancillary lumens, or a combination thereof.

Some embodiments of the present system comprise: a dressing the comprises: a connector the comprises: a connector body configured to define at least a portion of a first channel; a viewing member coupled to the connector body; and a deformable member positioned within the first channel and configured to deform based on a pressure of a cavity partially defined by the deformable member and to provide a visual indication, via the viewing member, of the pressure of the cavity; and a drape coupled to the connector and configured to be coupled to a tissue site; and a positive-pressure source configured to be coupled to the connector via one or more tubes. In some such implementations, the positive-pressure source is configured to provide pressurized oxygen to the dressing, and/or the positive-pressure source comprises an oxygen tank or an oxygen collector.

Some embodiments of the present methods comprise: providing, by an positive-pressure source, pressurized oxygen to a dressing coupled to a tissue site of a patient, where the dressing comprises: a connector that comprises: a connector body configured to define at least a portion of a first channel; a viewing member coupled to the connector body; and a deformable member positioned within the first channel and configured to deform based on a pressure of a cavity partially defined by the deformable member and to provide a visual indication, via the viewing member, of the pressure of the cavity; and a drape coupled to the connector and configured to be coupled to the tissue site; and responsive to the pressurized oxygen provided to the dressing, deforming the deformable member to indicate a positive-pressure state at the tissue site. In some implementations of the embodiments of the present methods, the methods further comprise responsive to excess pressurized oxygen provided to the dressing, deforming the pressure relief valve to form an opening in the dressing; and releasing the excess pressurized oxygen from the dressing via the opening.

As used herein, various terminology is for the purpose of describing particular implementations only and is not intended to be limiting of implementations. For example, as used herein, an ordinal term (e.g., "first," "second," "third," etc.) used to modify an element, such as a structure, a component, an operation, etc., does not by itself indicate any priority or order of the element with respect to another element, but rather merely distinguishes the element from another element having a same name (but for use of the ordinal term). The term "coupled" is defined as connected, although not necessarily directly, and not necessarily mechanically. Additionally, two items that are "coupled" may be unitary with each other. To illustrate, components may be coupled by virtue of physical proximity, being integral to a single structure, or being formed from the same piece of material. Coupling may also include mechanical, thermal, electrical, communicational (e.g., wired or wireless), or chemical coupling (such as a chemical bond) in some contexts.

The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. As used herein, the term "approximately" may be substituted with "within 10 percent of" what is specified. Additionally, the term "substantially" may be substituted with "within [a percentage] of" what is specified, where the percentage includes 0.1, 1, or 5 percent; or may be understood to mean with a design, manufacture, or measurement tolerance. The phrase "and/or" means and or. To illustrate, A, B, and/or C includes: A alone, B alone, C alone, a combination of A and B, a combination of A and C, a combination of B and C, or a combination of A, B, and C. In other words, "and/or" operates as an inclusive or.

The terms "comprise" (and any form of comprise, such as "comprises" and "comprising"), "have" (and any form of have, such as "has" and "having"), and "include" (and any form of include, such as "includes" and "including"). As a result, an apparatus that "comprises," "has," or "includes" one or more elements possesses those one or more elements, but is not limited to possessing only those one or more elements. Likewise, a method that "comprises," "has," or "includes" one or more steps possesses those one or more steps, but is not limited to possessing only those one or more steps.

Any aspect of any of the systems, methods, and article of manufacture can consist of or consist essentially of—rather than comprise/have/include—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb. Additionally, it will be understood that the term "wherein" may be used interchangeably with "where."

Further, a device or system that is configured in a certain way is configured in at least that way, but it can also be configured in other ways than those specifically described. The feature or features of one embodiment may be applied to other embodiments, even though not described or illustrated, unless expressly prohibited by this disclosure or the nature of the embodiments.

Some details associated with the aspects of the present disclosure are described above, and others are described below. Other implementations, advantages, and features of the present disclosure will become apparent after review of the entire application, including the following sections: Brief Description of the Drawings, Detailed Description, and the Claims.

BRIEF DESCRIPTION OF THE DRAWINGS

A further understanding of the nature and advantages of the present disclosure may be realized by reference to the following drawings. The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers.

FIGS. 6A-6E are each a top view of example indications of the connector of FIG. 2;

DETAILED DESCRIPTION

Figures 1A, 1B:
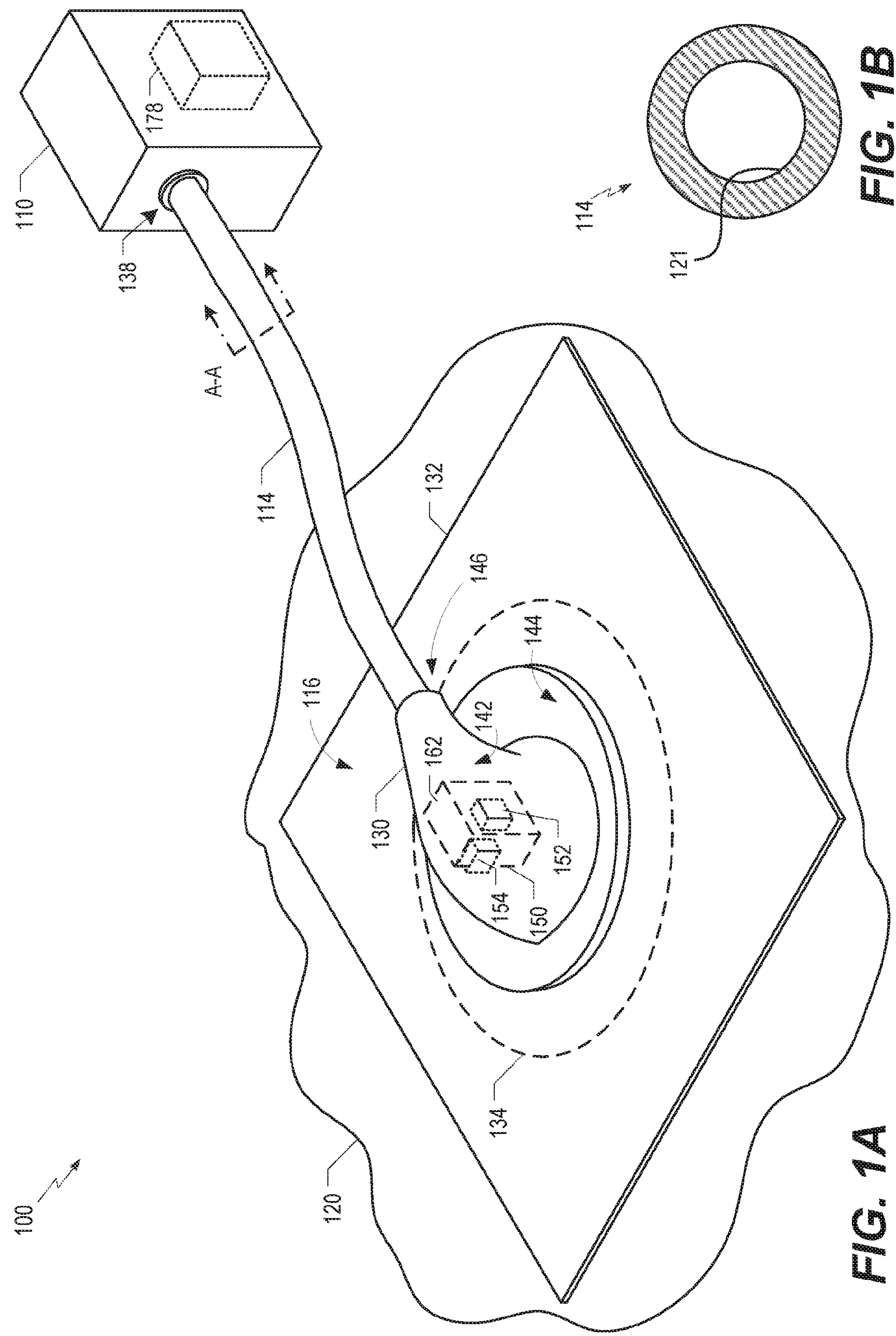
FIG. 1A is a perspective view of an example of a system for wound therapy.
FIG. 1B is a cross-sectional view of an example of a tube taken along line A-A of FIG. 1A.

As used herein, the terms "tissue site" and "target tissue" as used herein can broadly refer to a wound (e.g., open or closed), a tissue disorder, and/or the like located on or within tissue, such as, for example, bone tissue, adipose tissue, muscle tissue, neural tissue, dermal tissue, vascular tissue, connective tissue, cartilage, tendons, ligaments, and/or the like. The terms "tissue site" and "target tissue" as used herein can also refer to a surrounding tissue area(s) and/or areas of tissue that are not necessarily wounded or exhibit a disorder, but include tissue that would benefit from tissue generation and/or tissue that may be harvested and transplanted to another tissue location. The terms "tissue site" and "target tissue" may also include incisions, such as a surgical incision. In some implementations, "target tissue" may correspond or refer to a wound, and "tissue site" may correspond or refer to a tissue area(s) surrounding and including the target tissue. Additionally, the term "wound" as used herein can refer to a chronic, subacute, acute, traumatic, and/or dehisced incision, laceration, puncture, avulsion, and/or the like, a partial-thickness and/or full thickness burn, an ulcer (e.g., diabetic, pressure, venous, and/or the like), flap, and/or graft. A wound may include chronic, acute, traumatic, subacute, and dehisced wounds, partial-thickness burns, ulcers (such as diabetic, pressure, or venous insufficiency ulcers), flaps, grafts, and fistulas, for example.

The term "positive-pressure" (or "hyperbaric") as used herein generally refers to a pressure greater than a local ambient pressure, such as the ambient pressure in a local environment external to a sealed therapeutic environment (e.g., an internal volume). In most cases, this positive-pressure will be greater than the atmospheric pressure at which the patient is located. Alternatively, the positive-pressure may be greater than a hydrostatic pressure associated with tissue at the tissue site. Unless otherwise indicated, values of pressure stated herein are gauge pressures. References to increases in positive-pressure typically refer to an increase in absolute pressure, and decreases in positive-pressure typically refer to a decrease in absolute pressure. Additionally, the process of increasing pressure may be described illustratively herein as "applying", "delivering," "distributing," "generating", or "providing" positive-pressure, for example.

The term "reduced-pressure" (and "negative-pressure" or "hypobaric") as used herein generally refers to a pressure less than a local ambient pressure, such as the ambient pressure in a local environment external to a sealed therapeutic environment (e.g., an internal volume). In most cases, this reduced-pressure will be less than the atmospheric pressure at which the patient is located. Alternatively, the reduced-pressure may be less than a hydrostatic pressure associated with tissue at the tissue site. Unless otherwise indicated, values of pressure stated herein are gauge pressures. References to increases in reduced-pressure typically refer to a decrease in absolute pressure, and decreases in reduced-pressure typically refer to an increase in absolute pressure. Additionally, the process of reducing pressure may be described illustratively herein as "applying", "delivering," "distributing," "generating", or "providing" reduced-pressure, for example.

The term “fluid” may refer to liquid, gas, air, or a combination thereof. The term “fluid seal,” or “seal,” means a seal adequate to maintain a pressure differential (e.g., positive-pressure or reduced-pressure) at a desired site given the particular pressure source or subsystem involved. Similarly, it may be convenient to describe certain features in terms of fluid “inlet” or “outlet” in such a frame of reference. However, the fluid path may also be reversed in some applications, such as by substituting a reduced-pressure source (negative or hypobaric pressure source) for a positive-pressure source, and this descriptive convention should not be construed as a limiting convention.

FIG. 1A shows a perspective view of an illustrative system 100 (e.g., a hyperbaric oxygen therapy system) for oxygen therapy using positive-pressure. System 100 may include a therapy device 110, a tube 114, and a dressing 116. System 100 is configured to provide oxygen and positive-pressure at a tissue site 120 associated with a target area of a patient. For example, dressing 116 may be in fluid communication with tissue site 120 and may be in fluid communication with therapy device 110 via tube 114. In some implementations, system 100 may include one or more components commercially available through and/or from KCI USA, Inc. of San Antonio, Tex., U.S.A., and/or its subsidiary and related companies (collectively, “KCI”).

Therapy device 110 (e.g., a positive-pressure treatment apparatus) is configured to provide oxygen at a positive-pressure via tube 114 and dressing 116. For example, therapy device 110 may include a positive-pressure source 178, such as a pressurized oxygen container, an oxygen concentrator, or an oxygen collector (e.g., a pump and a filter) and/or the like, configured to be actuatable (and/or actuated) to apply positive-pressure (e.g., hyperbaric pressure) to dressing 116. In other implementations, positive-pressure source 178 is included in dressing 116 that includes connector 130, or positive-pressure source 178 is external to dressing 116, included in connector 130, and coupled to dressing 116 via connector 130. As illustrative, non-limiting examples, positive-pressure applied to a tissue site may typically ranges between 5 millimeters mercury (mm Hg) (667 pascals (Pa)) and 30 mm Hg (4.00 kilo (k) Pa). Common therapeutic ranges are between 10 mm Hg (1.33 kPa) and 25 mm Hg (3.33 kPa).

Figure 7:
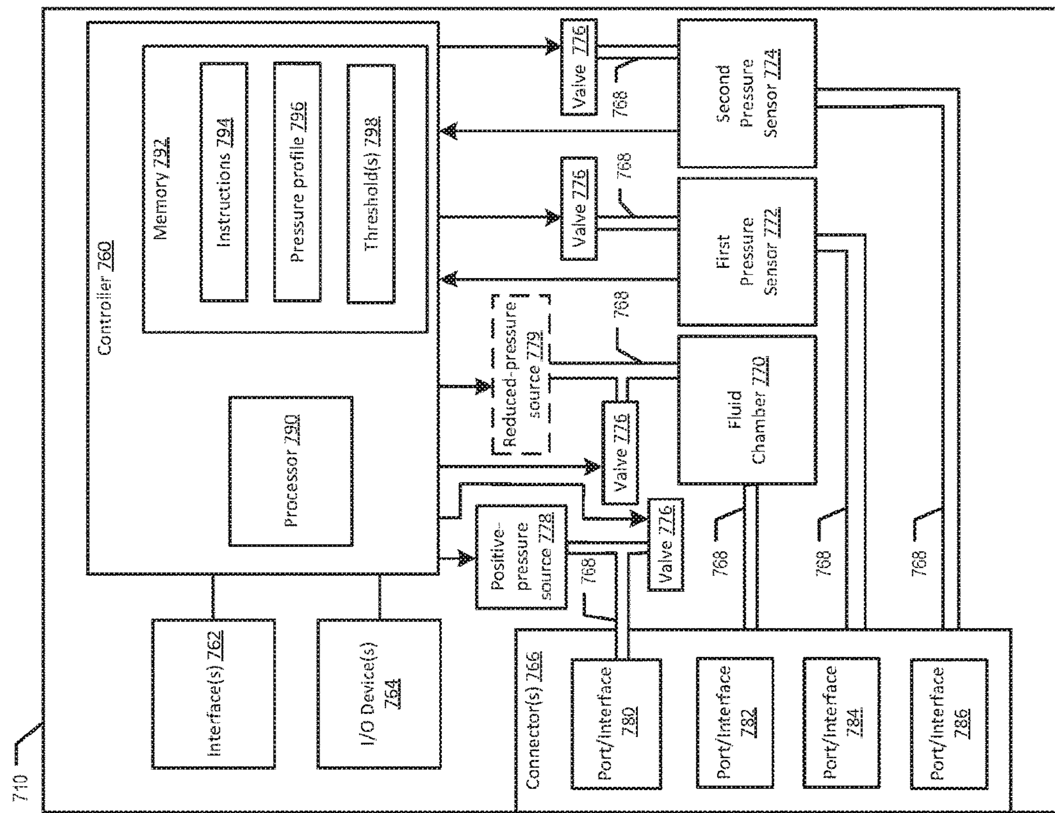
FIG. 7A is diagram of an example a system for wound therapy.
FIG. 7B is a cross-sectional view of an example of a tube taken along line B-B of FIG. 7A.

In some implementations, as described further with reference to FIG. 7A, the therapy device 110 includes a reduced-pressure source, such as a vacuum source (e.g., a pump and/or the like), configured to be actuatable (and/or actuated) to apply reduced-pressure (e.g., negative pressure) to the dressing 116. In such implementations, therapy device 110 may alternate between providing positive-pressure therapy and negative-pressure therapy to the dressing 116, may provide positive-pressure therapy to a first portion of the dressing 116 and negative-pressure therapy to a second portion of the dressing 116, may provide no positive or negative pressure, or a combination thereof. In some such implementations, the therapy device 110 can provide positive-pressure therapy and negative-pressure therapy to the dressing 116 at the same time (e.g., partially concurrently). As illustrative, non-limiting examples, reduced-pressure applied to a tissue site may typically ranges between −5 millimeters mercury (mm Hg) (−667 pascals (Pa)) and −500 mm Hg (−66.7 kilo (k) Pa). Common therapeutic ranges are between −75 mm Hg (−9.9 kPa) and −300 mm Hg (−39.9 kPa).

Therapy device 110 may also include one or more other components, such as a sensor, a processing unit (e.g., a processor), an alarm indicator, a memory, a database, software, a display device, a user interface, a regulator, and/or another component, that further facilitate positive-pressure therapy. Additionally, or alternatively, therapy device 110 may be configured to receive fluid, exudate, and or the like via dressing 116 and tube 114. Therapy device 110 may include one or connectors, such as a representative connector 138. Connector 130 is configured to be coupled to tube 114. Additionally, or alternatively, therapy device 110 may include one or more sensors, such a pressure sensor (e.g., a pressure transducer). The one or more sensors may be configured to enable therapy device 110 to monitor and/or sense a pressure associated with tube 114 and/or dressing 116. An illustrative example of therapy device 110 is described further herein at least with reference to FIG. 7A.

As used herein, a “tube” broadly refers to a tube, pipe, hose, conduit, or other structure with one or more lumens adapted to convey fluid, exudate, and/or the like, between two ends. In some implementations, a tube may be an elongated, cylindrical structure with some flexibility; however, a tube is not limited to such a structure. Accordingly, tube may be understood to include a multiple geometries and rigidity. Tube 114 includes one or more lumens (e.g., one or more through conduits), such as a single lumen conduit or multiple single-lumen conduits. Tube 114 (e.g., a least one of the one or more lumens) is configured to enable fluid communication between therapy device 110 and dressing 116. For example, fluid(s) and/or exudate can be communicated between therapy device 110 and dressing 116, and/or one or more pressure differentials (e.g., positive-pressure, negative pressure, or both) can be applied by therapy device 110 to dressing 116. As an illustrative, non-limiting illustration, tube 114 is configured to deliver at least pressurized oxygen from therapy device 110 to dressing 116 to establish positive-pressure. Communication of fluid(s) and application of a pressure differential can occur separately and/or concurrently.

In some implementations, tube 114 may include multiple lumens, such as a primary lumen (e.g., a positive-pressure/fluid lumen) for application of positive-pressure and/or communication of fluid, and one or more secondary lumens proximate to or around the primary lumen. The one or more secondary lumens (e.g., one or more ancillary/peripheral lumens) may be coupled to one or more sensors (of therapy device 110), coupled to one or more valves, as an illustrative, non-limiting example. Although tube 114 is described as a single tube, in other implementations, system 100 may include multiple tubes, such as multiple distinct tubes coupled to therapy device 110, dressing 116, or both.

Referring to FIG. 1B, an illustrative example of a cross-section of tube 114 (in which tube 114 comprises a single lumen) along line A-A of FIG. 1A is shown. Tube 114 may include a primary lumen 121 (e.g., a positive-pressure/fluid lumen). In other implementations, tube 114 may include one or more secondary lumens, such as a negative-pressure/fluid lumen, one or more sense lumens, etc., or a combination thereof, such as described with reference to at least FIG. 7B. Although tube 114 has been described and/or shown as having a circular cross-sectional shape, in other implementations, tube 114 may have a cross-sectional shape other than a circle, such as an oval, triangle, quadrilateral, pentagon, star, or another shape, as illustrative, non-limiting examples.

Referring to FIG. 1A, dressing 116 includes a connector 130 (also referred to as a dressing connection pad or a pad), a drape 132, and a manifold 134 (also referred to as a distribution manifold or an insert). Drape 132 may be coupled to connector 130. To illustrate, drape 132 may be coupled to connector 130 via an adhesive, a separate adhesive drape over at least a portion of connector 130 and at least a portion of drape 132, or a combination thereof, as illustrative, non-limiting examples.

Drape 132 may be configured to couple dressing 116 at tissue site 120 and/or to provide a seal to create an enclosed space (e.g., an interior volume) corresponding to tissue site 120. For example, drape 132 may be configured to provide a fluid seal between two components and/or two environments, such as between a sealed therapeutic environment and a local ambient environment. To illustrate, when coupled to tissue site 120, drape 132 is configured to maintain a pressure differential (provided by a positive-pressure source 178 or a negative-pressure source) at tissue site 120. Drape 132 may include a drape aperture that extends through drape 132 to enable fluid communication between device and target tissue, as describe further with reference to FIG. 7A. Drape 132 may be configured to be coupled to tissue site 120 via an adhesive, such as a medically acceptable, pressure-sensitive adhesive that extends about a periphery, a portion, or an entirety of drape 132. Additionally, or alternatively, drape 132 may be coupled to tissue site 120 via a double-sided drape tape, paste, hydrocolloid, hydrogel, and/or other sealing device or element, as illustrative, non-limiting examples.

Drape 132 may include an impermeable or semi-permeable, elastomeric material, as an illustrative, non-limiting example. In some implementations, drape 132 may be liquid/gas (e.g., moisture/vapor) impermeable or semi-permeable. "Elastomeric" means having the properties of an elastomer. For example, elastomer generally refers to a polymeric material that may have rubber-like properties. More specifically, an elastomer may typically have ultimate elongations greater than or equal to 100% and a significant amount of resilience. The resilience of a material refers to the material's ability to recover from an elastic deformation. Elastomers that are relatively less resilient may also be used as these elastomers. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane (PU), EVA film, co-polyester, and silicones. In some implementations, drape 132 may include the "V.A.C.® Drape" commercially available from KCI. Additional, specific non-limiting examples of materials of drape 132 may include a silicone drape, 3M Tegaderm® drape, and a polyurethane (PU) drape such as one available from Avery Dennison Corporation of Pasadena, Calif. An additional, specific non-limiting example of a material of the drape 132 may include a 30 micrometers (μm) matt polyurethane film such as the Inspire™ 2317 manufactured by Exopack™ Advanced Coatings of Matthews, N.C.

Manifold 134 is configured to be positioned on and/or near tissue site 120, and may be secured at the tissue site 120, such as secured by drape 132. The term "manifold" as used herein generally refers to a substance or structure that may be provided to assist in applying a pressure differential (e.g., positive-pressure differential) to, delivering fluids to, or removing fluids and/or exudate from a tissue site and/or target tissue. The manifold typically includes a plurality of flow channels or pathways that distribute fluids provided to and removed from the tissue site. In an illustrative implementation, the flow channels or pathways are interconnected to improve distribution of fluids provided to or removed from the tissue site. Manifold 134 may be a biocompatible material that may be capable of being placed in contact with the tissue site and distributing positive and/or negative-pressure to the tissue site. Manifold 134 may include, without limitation, devices that have structural elements arranged to form flow channels, such as foam, cellular foam, open-cell foam, porous tissue collections, liquids, gels, and/or a foam that includes, or cures to include, flow channels, as illustrative, non-limiting examples. Additionally, or alternatively, manifold may include polyethylene, a polyolefin, a polyether, polyurethane, a co-polyester, a copolymer thereof, a combination thereof, or a blend thereof.

In some implementations, manifold 134 is porous and may be made from foam, gauze, felted mat, or other material suited to a particular biological application. In a particular implementation, manifold 134 may be a porous foam and may include a plurality of interconnected cells or pores that act as flow channels. The foam (e.g., foam material) may be either hydrophobic or hydrophilic. As an illustrative, non-limiting example, the porous foam may be a polyurethane, open-cell, reticulated foam such as GranuFoam® material manufactured by Kinetic Concepts, Incorporated of San Antonio, Tex.

In some implementations, manifold 134 is also used to distribute fluids such as medications, antibacterials, growth factors, and other solutions to the tissue site. Other layers may be included in or on manifold 134, such as absorptive materials, wicking materials, hydrophobic materials, and hydrophilic materials. In an implementation in which the manifold 134 includes a hydrophilic material, manifold 134 may be configured to wick fluid away from tissue site 120 and to distribute positive-pressure to tissue site 120. The wicking properties of manifold 134 may draw fluid away from the tissue site 120 by capillary flow or other wicking mechanisms. An illustrative, non-limiting example of a hydrophilic foam is a polyvinyl alcohol, open-cell foam such as V.A.C. WhiteFoam® dressing available from Kinetic Concepts, Inc. of San Antonio, Tex. Other hydrophilic foams may include those made from polyether and/or foams that have been treated or coated to provide hydrophilicity.

In some implementations, manifold 134 is constructed from bioresorbable materials that do not have to be removed from tissue site 120 following use of the system 100. Suitable bioresorbable materials may include, without limitation, a polymeric blend of polylactic acid (PLA) and polyglycolic acid (PGA). The polymeric blend may also include without limitation polycarbonates, polyfumarates, and capralactones. Manifold 134 may further serve as a scaffold for new cell-growth, or a scaffold material may be used in conjunction with manifold 134 to promote cell-growth. A scaffold may be a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials. Although a manifold 134 is illustrated in FIG. 1A, in other implementations, dressing 116 does not include manifold 134. In such implementations, drape 132 of dressing 116 is coupled to connector 130.

Connector 130 includes a body 142 (e.g., housing) and a base 144, and is configured to be coupled to tube 114 via an interface 146 (e.g., a port). Base 144 is configured to be coupled to dressing 116. For example, base 144 may be coupled, such as via an adhesive, to drape 132 and/or manifold 134. In some implementations, base 144 comprises a flange that is coupled to an end of body 142 and/or is integrally formed with body 142. Connector 130, such as body 142, base 144, interface 146, or a combination thereof, may be made of rigid material and/or a semi-rigid material. In a non-limiting example, connector 130 may be made from a plasticized polyvinyl chloride (PVC), polyurethane, cyclic olefin copolymer elastomer, thermoplastic elastomer, poly acrylic, silicone polymer, or polyether block amide copolymer. In some implementations, connector 130 is formed of a semi-rigid material that is configured to expand when under a force, such as positive-pressure greater than or equal to a particular amount of pressure. Additionally or alternatively, connector 130 may be formed of a semi-rigid material that is configured to collapse when under a force, such as reduced-pressure less than or equal to a threshold pressure.

Body 142 includes one or more channels or one or more conduits that extend from and/or are coupled to interface 146. To illustrate, body 142 may include a primary channel configured to be coupled in fluid communication with a primary lumen (e.g., 121) of tube 114. The primary channel may be coupled to a cavity (e.g., a tissue cavity partially defined by body 142) having an aperture open towards manifold 134 (and/or towards tissue site 120). For example, the primary channel may include a first opening associated with interface 146 and a second opening (distinct from the aperture of the cavity) associated with the cavity. Thus, the primary channel may define a through channel of body 142 to enable fluid communication between interface 146 and tissue site 120.

Body 142 includes a channel 150 (e.g., a through channel) having a first aperture open opposite dressing 116 and a second aperture open towards dressing 116. For example, the first aperture is located on an outer surface side (e.g., an ambient environment surface) of connector 116 and the second aperture is located on an inner surface side (e.g., a tissue facing side) of connector 116. The second aperture is configured to be coupled to one or more lumens of tube 114, such as coupled via the cavity. A deformable member 152 is positioned within channel 150 and configured to at least partially deform responsive to positive-pressure applied to a cavity defined by deformable member 152. Deformable member 152 is configured to provide a visual indication, via a viewing member 162 of body 142, of the pressure of the cavity. Deformable member 152 may be coupled to body 142. To illustrate, deformable member 152 may be coupled to body 142 via an adhesive (e.g., glue, epoxy, etc.), RF welding, heat welding, ultrasonic welding, or insert molded, as illustrative, non-limiting examples.

Deformable member 152 may include an expandable member or structure, such as a flexible polymer member. Deformable member 152 may be coupled to or encased in channel 150 such that deformable member 152 divides the channel 150 into multiple cavities (e.g., a tissue cavity and a deformation cavity) (not shown), as described further with reference to FIGS. 2-5. Deformable member 152 is in contact with dressing 116 pneumatically. In some implementations, deformable member 152 is pneumatically coupled to ambient pressure. For example, dressing 116 and/or viewing member 162 (e.g., window) has an aperture to allow ambient air to enter the deformation cavity, which causes a pressure differential between the tissue cavity, and the deformation cavity thereby enables the deformable member 152 to deform responsive to pressure in the tissue cavity. To illustrate, responsive to positive-pressure, as compared to ambient pressures, deformable member 152 deforms such that the tissue cavity enlarges in size and the deformation cavity reduces in size. As pressure increases, deformable member 152 deforms to come in contact with viewing member 162 and becomes visible or more clearly visible to a patient or care provider. In some implementations, deformable member 152 is colored or has one or more markings. For example, the deformable member 152 includes one or more colors or markings to indicate one or more positive-pressure states, as described further with reference to FIGS. 6A-6E.

Deformable member 152 includes a flexible or compliant material, such as an elastomer, which is configured to deform under positive-pressure, such as when positive-pressure in the connector 130 exceeds a threshold. For example, deformable member 152 may be configured to deform to provide the visual indication between 10 mm Hg and 25 mm Hg. For example, deformable member 152 may be configured to provide the visual indication at least at or greater than, or substantially equal to any one of, or between two of: 10, 12, 15, 18, 19, 20, 21, 22, 23, 24, 25, 26, 27, 28, 30, 31, 32, 33, or 35 mm Hg. The visual indication may indicate oxygen therapy is being provided at a level which promotes healing. Deforming to an extent such that a visual indication is provided may be referred to as deforming to a state or transitioning between states. As another example, deformable member 152 may be configured to deform to provide the visual indication at pressures above 15 mm Hg. To illustrate, deformable member 252 begins deforming at less than 15 mm Hg, and at 15 mm Hg, deformable member 252 deforms to such a degree or extent that deformable member 252 provides the visual indication. In other implementations, deformable member 252 deforms to such a degree or extent that deformable member 252 provides the visual indication at 20 mm Hg or above, 22 mm Hg or above, 25 mm Hg or above, etc. Thus, the visual indication may be associated with any pressure that is greater than a threshold pressure. In some implementations, the visual indication is associated with a specific range of pressures, and a second visual indication is associated with a second range of pressures. As illustrative, non-limiting examples, the range of pressures may include one of 10-20, 10-22, 12-18, 12-24, 15-18, 15-20, 20-25 mm Hg, etc., and the second range of pressures may include one of 20-25, 20-30, 25-35, greater than 22, greater than 25 mm Hg, etc. In some implementations, the second range of pressures may include at least at or greater than, or substantially equal to any one of, or between two of: 18, 19, 20, 21, 22, 23, 24, 25, 26, 27, 28, 30, 31, 32, 33, or 35 mm Hg.

In some implementations, deformable member 152 has a hardness of 10 Shore A to 20 Shore A or includes a material that has a hardness of 10 Shore A to 20 Shore A. As illustrative, non-limiting examples, deformable member 152 comprises a silicone elastomer material, a fluorosilicone material, an ethylene propylene diene terpolymer (EPDM) material, a nitrile butadiene rubber (NBR) material, a thermoplastic elastomer material (e.g., Hytrel a registered trademark of E. I. Du Pont De Nemours and Company), a polyether block amide material (e.g., PEBAX a registered trademark of Arkema, Inc.), or a polyurethane (PU) material. Illustrative, non-limiting examples of commercially available connectors into which channel 150 and deformable member 152 can be incorporated include a "V.A.C. T.R.A.C.® Pad," or "Sensa T.R.A.C.® Pad" available from Kinetic Concepts, Inc. (KCI) of San Antonio, Tex.

Connector 130 further includes viewing member 162. Viewing member 162 is coupled to body 142 or comprises a portion of body 142. Viewing member 162 is configured to enable viewing of deformable member 152. For example, viewing member 162 is positioned in channel 150 or on top of channel 150. In some implementations, viewing member 162 includes or corresponds to a transparent material or a translucent material such that deformable member 152 is visible through viewing member 162 or at least partially occluded by viewing member 162 depending on a deformation degree or state of deformable member 152. In other implementations, viewing member 162 includes or corresponds to frosted glass and is semi-opaque. Additionally, viewing member 162 may include or correspond to a first material that is different from a second material of deformable member 152 such that the second material does not adhere to the first material when deformable member 152 contacts the viewing member 162.

In some implementations, connector 130 further includes pressure relief valve 154. For example, body 242 may define at least a portion of one or more cavities, such as a second channel, into which a pressure relief valve 254 is positioned. Pressure relief valve 154 is configured to configured to enable flow when the pressure of the cavity is greater than equal to a threshold value. When the pressure of the cavity is less than the threshold value, the pressure relief valve is configured to restrict fluid from exiting the connector 130 (e.g., the second channel thereof), and when the pressure of the cavity is great than or equal to the threshold value, the pressure relief valve is configured to enable fluid to exit from the connector 130. Pressure relief valve 154 includes a flexible or compliant material which is configured to deform and/or move under positive-pressure at the threshold value. As an illustrative, non-limiting example, pressure relief valve 154 is configured to deform and/or move to enable fluid to exit from connector 130 at a pressure between 22 mm Hg and 35 mm Hg. Enabling fluid flow from connector 130 at pressures between 22 mm Hg and 35 mm Hg may prevent capillary closure and reduction of efficiency of oxygen therapy. In some implementations, pressure relief valve 154 has a hardness of 40 Shore A to 60 Shore A or includes a material that has a hardness of hardness of 40 Shore A to 60 Shore A. As illustrative, non-limiting examples, pressure relief valve 154 comprises a silicone elastomer material, a fluorosilicone material, an ethylene propylene diene terpolymer (EPDM) material, a nitrile butadiene rubber (NBR) material, a thermoplastic elastomer material (e.g., Hytrel a registered trademark of E. I. Du Pont De Nemours and Company), a polyether block amide material (e.g., PEBAX a registered trademark of Arkema, Inc.), or a polyurethane (PU) material. Although FIG. 1A is illustrated as including pressure relief valve 154, in other implementations, connector 130 does not include pressure relief valve 154.

During operation of system 100, dressing 116 is coupled to tissue site 120. Additionally, dressing 116 is coupled to device 110 via tube 114. Positive-pressure can be applied to dressing 116 (e.g., an interior volume of dressing 116) by a positive-pressure source 178 associated with device 110. If device 110 is coupled to dressing 116 such that positive-pressure is not provided to channel 150 (i.e., a portion thereof) and/or tissue site 120, deformable member 152 maintains an undeformed state (e.g., a first state) which indicates that positive pressure or oxygen therapy is not being applied to channel 150 (i.e., a portion thereof) and/or tissue site 120. In such situations, a patient or care provider can read the indication without a power source (e.g., electricity).

Additionally, when positive-pressure is not provided to channel 150 and/or tissue site 120, pressure relief valve 154 obstructs or restricts fluid communication between channel 150 and ambient air, and/or between tissue site 120 and ambient air, via the pressure relief valve 154 (e.g., an aperture thereof) is obstructed/restricted.

Alternatively, if device 110 is coupled to a positive-pressure source 178 such that positive-positive is provided to channel 150, deformation of deformable member 152 occurs (e.g., an increase in a degree or amount of deformation of deformable member 152) to provide a visual indication (e.g., cause an increase in visibility of deformable member 152 through viewing member 162). When deformable member 152 deforms to such a degree to provide the visual indication, the deformable member 152 is in a deformed state (e.g., a second state). The visual indication and/or second state may indicate positive-pressure or oxygen therapy is being applied to tissue site 120. Additionally, when positive-pressure is provided to channel 150, pressure relief valve 154 maintains its shape and/or position and obstructs or restricts fluid communication between channel 150 and ambient air, and/or between tissue site 120 and ambient air, via the pressure relief valve 154 (e.g., an aperture thereof). In such situations, positive-pressure is maintained at tissue site 120.

Additionally, when excess positive pressure is applied at tissue site 120 (e.g., when positive-pressure exceeds a threshold pressure value), pressure relief valve 154 causes or enables fluid communication between tissue site 120 and ambient air. For example, the pressure relief valve 154 deforms or moves under excess pressure to form an aperture which releases fluid from channel 150 and/or tissue site 120 to ambient air to reduce or limit an amount of positive-pressure at the tissue site 120. By pressure relief valve 154 reducing/limiting the amount of positive-pressure (e.g., releasing or bleeding excess positive-pressure) at the tissue site 120, excess positive-pressure at tissue site 120 may be avoided. In some implementations, when positive-pressure exceeds a threshold pressure value, the deformable member 152 deforms further (relative to an amount of deformation associated with visual indication) to provide a second visual indication. For example, the deformable member 152 deforms to transition to an over-deformed state or a fully-deformed state (e.g., a third state), and deformable member 152 indicates an overpressurized state. Alternatively, a second deformable member (e.g., similar to deformable member 152) may be incorporated into body 142 and configured to indicate an overpressurized state. Avoiding overpressurized states may increase wound recovery by avoiding an overpressurized state in which capillaries of tissue site 120 may begin to close.

Furthermore, in some implementations, reduced-pressure can be applied to dressing 116 (e.g., the interior volume of dressing 116 or a second interior volume of the dressing 116) by a reduced-pressure source associated with device 110. One or more additional deformable members 152 can be used to provide visual indications associated with reduced pressure and/or indicate states of reduced-pressure, such as a neutral pressure state (e.g., a barometric pressure state), a negative-pressure state (e.g., a hypobaric pressure state), and an excess negative-pressure state, etc.

In a particular implementation, dressing 116 includes connector 130 and drape 132 coupled to the connector 130 and is configured to be coupled to tissue site 120. Connector 130 may include body 142 (e.g., a connector body) configured to define at least a portion of a first channel (e.g., 150). Connector 130 may also include a conduit coupled to (or defined by) body 142. Deformable member 152 may be configured to be transitionable between a first state and a second state, where, when the deformable member is in a first state, deformable member 152 is configured to indicate a first pressure state (e.g., barometric pressure or a lack of operational/positive pressure), and when deformable member 152 is in the second state, deformable member 152 is configured to a second pressure state, such as hyperbaric pressure, operational pressure, or overpressure. For example, deformable member 152 may be positioned within the cavity (e.g., 150) and be configured in a first state (when exposed to ambient pressure). When deformable member 152 is exposed to positive-pressure, deformable member 152 is configured deform to transition to the second state. For example, as pressure increases in the cavity (e.g., 150) the deformable member 152 experiences elastic deformation and becomes visible to a patient or care provided via viewing member 162 of the connector 130.

In another particular implementation, connector 130 includes connector body 142 configured to define at least a portion of a first channel (e.g., 150); viewing member 162 coupled to the connector body 142; and deformable member 152 positioned within the first channel and configured to deform based on a pressure of a cavity (e.g., a tissue cavity 350B of FIG. 3) partially defined by the deformable member 152 and to provide a visual indication, via viewing member 162, of the pressure of the cavity. In some implementations, connector 130 further includes pressure relief valve 154 positioned within a second channel (e.g., second channel 256 of FIG. 2) defined by the connector body 142 and configured to enable flow when the pressure of the cavity is greater than equal to a threshold value.

Thus, connector 130 (e.g., deformable member 152) is configured to mechanically indicate a positive pressure state and connector 130 (e.g., pressure relief valve 154) is configured to provide a flow path to reduce or limit an amount of positive-pressure at the tissue site 120 when excess positive-pressure is provided to channel 150 and/or tissue site 120. To illustrate, when positive-pressure is applied to a tissue cavity of channel 150 and tissue site 120, deformable member 152 deforms to provide a visual indication (mechanical indication) that positive-pressure is being applied to the channel 150 and/or the tissue site 120. Accordingly, deformable member 152 enables mechanical pressure indication with flexible materials without using and/or independent of electronic pressure indication devices or requiring power. If excess positive-pressure is applied to channel 150, pressure relief valve 154 may deform to provide an aperture, thereby avoiding or limiting excess positive-pressure and/or capillary constriction at tissue site 120. Accordingly, deformable member 152 and/or pressure relief valve 154 may enable effective, efficient, and safe positive-pressure therapy through use of system 100, thereby advancing patient reliability and confidence in the treatment.

Referring to FIGS. 2-5, examples of a connector 230 are shown. For example, connector 230 may include or correspond to connector 130. Connector 230 is configured to be incorporated in or coupled to a dressing, such as a dressing of a positive-pressure system. For example, the dressing may include or correspond to dressing 116 of system 100.

Figure 2:
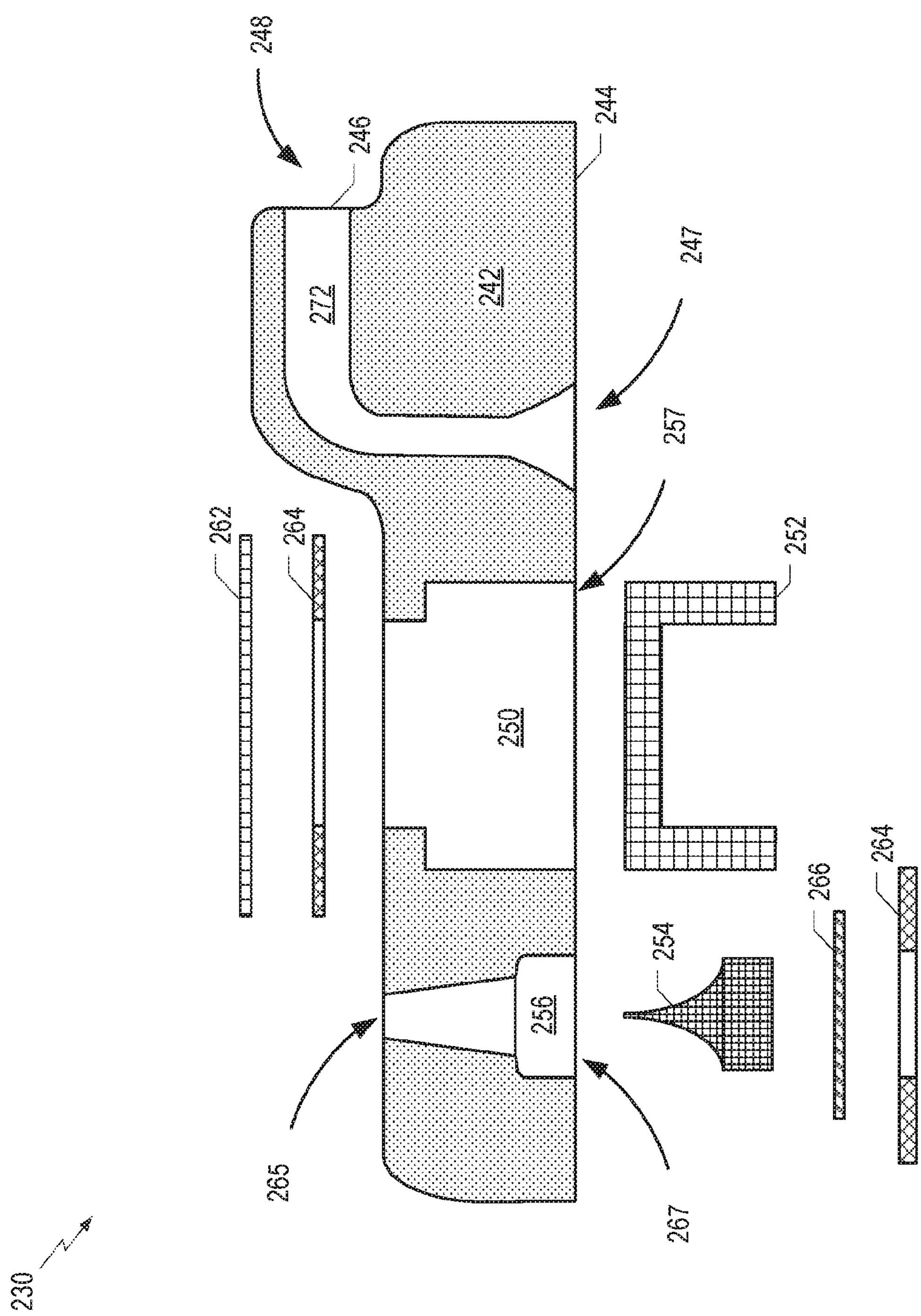
FIG. 2 is an exploded cross-sectional view of an example of a connector.

Referring to FIG. 2, an example of an exploded cross-section view of connector 230 is shown. Connector 230 includes a connector body 242 (e.g., housing), a base 244, and an interface 246 (e.g., a port). Connector body 242 may include or correspond to body 142. Base 244 and interface 246 may include or correspond to base 144 and interface 146.

Connector 230 may include a first end 247 that corresponds to base 244 and a second end 248 that corresponds to interface 246. Connector 230 (e.g., connector body 242) may be configured to be coupled to a tissue site (e.g., 120) via first end 247 of body 242 and may be configured to be coupled to a positive-pressure source (e.g., 178) via second end 248 of body 242.

Connector 230 is configured to be coupled to a tube (not shown in FIG. 2) via interface 246. For example, interface 246 is sized to be coupled to tube 114 of FIG. 1A. Although not illustrated in FIG. 2, connector 130 (e.g., interface 246) may include couplers or other features, such as a ridge, to facilitate coupling to the tube. As illustrated in FIG. 2, body 242 includes conduit 272 in fluid connection with interface 246 and extending from first end 247 to second end 248. Conduit 272 is configured to provide fluid flow between tissue site (e.g., 120) and interface 246. In other implementations, body 242 defines a channel that provides fluid flow between tissue site (e.g., 120) and interface 246.

Body 242 may define at least a portion of one or more channels, such as a first channel 250, into which a deformable member 252 is positioned, and a second channel 256, into which a pressure relief valve 254 is positioned. First channel 250 and deformable member 252 may include or correspond to channel 150 and deformable member 152, respectively. Pressure relief valve 254 may include or correspond to pressure relief valve 154. First channel 250 may have an opening 257 that corresponds to interface 246. For example, opening 257 is in fluid communication with interface 246 via conduit 272. To illustrate, opening 257 is in fluid communication with conduit 272 via a cavity (e.g., a tissue cavity) partially defined by a tissue site and body 242.

Figure 3:
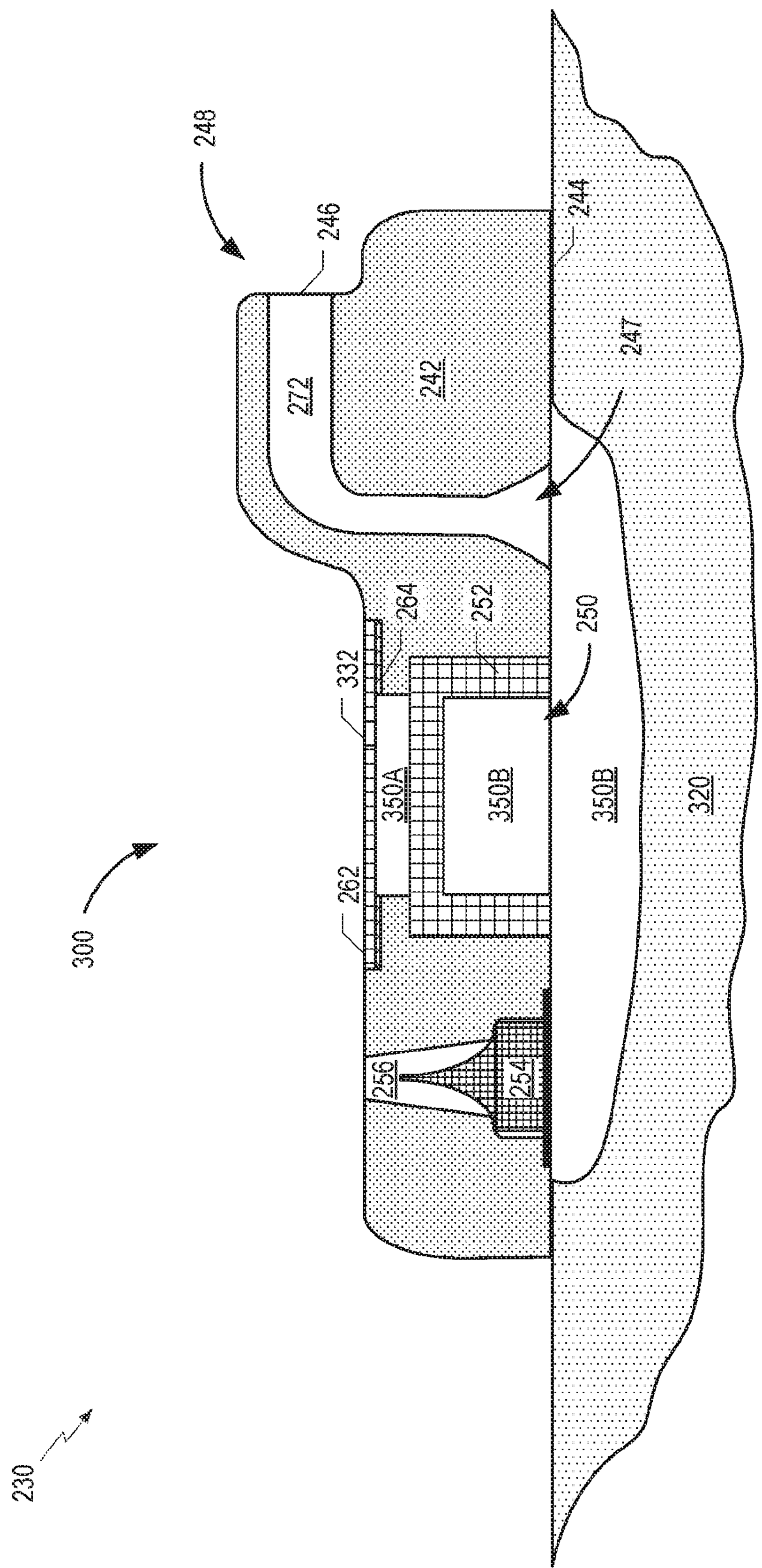
FIG. 3 is a cross-sectional view of the example of the connector of FIG. 2 in a first state.

Insertion of the deformable member 252 into first channel 250 may create (e.g., subdivide first channel 250 into) one or more cavities in the first channel 250, such as an upper cavity (e.g. a first cavity) and a lower cavity (e.g., a second cavity), as described further with reference to FIG. 3. The upper and lower cavities are not in fluid connection with one another and are divided by and defined in part by deformable member 252. The lower cavity of the first channel 250 and the opening 257 may be in fluid communication with a tube coupled to interface 246, such as via the conduit 272.

Body 242 further includes or is coupled to window 262. Window 262 may include or correspond to viewing member 162 of FIG. 1. Window 262 includes or corresponds to a transparent material or a translucent material and is configured to enable viewing of deformable member 252 through the window 262. For example, the window 262 enables viewing of deformable member 252 in the second state and at least partially occludes viewing of deformable member in the first state. As an illustrative, non-limiting example, the window 262 comprises frosted glass and is semi-opaque. The upper cavity of the first channel 250 may be defined in part by window 262. In some implementations, window 262 is coupled to body 242 via adhesive 264 (e.g. a layer or ring of adhesive material, such as a first adhesive ring). In a particular implementation, the upper cavity of the first channel 250 is in fluid connection with ambient air via a through hole or aperture (not shown) in the window 262, as described with reference to FIG. 3.

Second channel 256 includes apertures 265, 267. Aperture 265 is positioned opposite first end 247 of connector body 242; aperture 267 is positioned at first end 247 of connector body 242. Apertures 265, 267 are in fluid communication with each other via second channel 256. Insertion of pressure relief valve 254 into second channel 256 may block fluid connection between apertures 265, 267, as described further with reference to FIG. 3. When pressure relief valve 254 is inserted into or positioned within second channel 256, the second channel 256 and the aperture 267 may be in fluid connection with a tube coupled to interface 246, such as via the tissue cavity and conduit 272.

In some implementations, pressure relief valve 254 is coupled to body 242 via adhesive 264 (e.g. a layer or ring of adhesive material, such as a second adhesive ring). Additionally, a filter 266 may be positioned proximate to the pressure relieve valve 254 and configured to filter fluid from the tissue site and cavity. For example, filter 266 is configured to prevent or reduce liquids (e.g., exudate) in the tissue cavity from entering the second channel 256. Filter 266 may correspond to a hydrophobic filter and may include a hydrophobic material or coating.

In some implementations, body 242 may include one or more conduits (e.g., channels) in addition to conduit 272. For example, body 242 may include a second channel in fluid communication with first channel 250, second channel 256, or both. To illustrate, second channel may provide negative-pressure and facilitate removal and/or drainage of exudate.

Referring to FIG. 3, an example of a cross-section view of connector 230 is shown in a first state 300 (e.g., a non-operational state). In FIG. 3, connector 230 is attached to a tissue site 320 and deformable member 252 is positioned in first channel 250. Tissue site 320 may include or correspond to tissue site 120. When deformable member 252 is positioned in first channel 250, deformable member 252 partially defines a deformation cavity 350A in first channel 250. Deformation cavity 350A is further defined by body 242 and window 262. When connector 230 is attached to tissue site 320, tissue site 320, body 242, and deformable member 252 define a tissue cavity 350B. Tissue cavity 350B is in fluid connection with interface 246 via conduit 272. Tissue cavity 350B is not in fluid connection with deformation cavity 350A, i.e., deformable member 252 provides a fluid barrier between cavities 350A, 350B. Thus, a pressure differential can form between deformation cavity 350A and tissue cavity 350B.

As shown, when connector 230 is in the first state 300, deformable member 252 is undeformed (e.g., in the first state) and does not provide a visual indication, such that the visual indication is not visible via window 262 or is partially occluded by window 262. However, by not providing the visual indication, deformable member 252 can still provide an indication of status and/or pressure, i.e., lack of a particular visual indication is an indication of a pressure less than or equal to a pressure associated with providing the visual indication. For example, when the deformable member 252 is undeformed and in the first state, the deformable member 252 is not visible or only partially visible through the window 262 and indicates a neutral pressure state (e.g., a barometric pressure state). To illustrate, the deformable member 252 does not contact the window 262 and an outline of the deformable member 252 is not clearly defined, e.g., does not form a ring or other shape on a surface of the window 262. Additionally or alternatively, a color, a marking or a portion of the deformable member 252 is not visible through the window 262.

In FIG. 3, when pressure relief valve 254 is exposed to ambient pressure in the tissue cavity 350B, pressure relief valve 254 is configured to obstruct or restrict fluid communication through the second channel 256 between tissue site 320 and ambient air. To illustrate, no pressure differential exists between the tissue site 320 (e.g., a pressure within tissue cavity 350B) and ambient air or a relatively small pressure differential exists between the tissue site 320 and ambient air such that a force generated by the pressure differential does not exceed a threshold force which causes the pressure relief valve 254 to deform. In the example illustrated in FIG. 3, the pressure relief valve 254 comprises a duckbill valve and a distal or top end of the duckbill valve remains closed. When the pressure relief valve 254 is undeformed and is obstructing or restricting flow, the pressure relief valve 254 indicates a lack of an excess pressure state or over-pressurized state. For example, the pressure relief valve 254 as shown indicates that capillaries of the tissue site 320 are open and/or are not closed. In other implementations, the pressure relief valve 254 comprises an umbrella valve, a combination duckbill umbrella valve, or another flexible pressure relief valve.

In some implementations window 262 and/or connector body 242 may include a through hole 332 (e.g., an aperture) positioned to enable fluid communication between the deformation cavity 350A and ambient air. For example, the deformation cavity 350A can freely equalize (e.g., reach equilibrium pressure) with ambient air. To illustrate, when deformable member 252 is exposed to ambient pressure in the deformation cavity 350A and ambient pressure in the tissue cavity 350B, as shown in FIG. 3, deformable member 252 is in a first state (e.g., an undeformed state) and is configured to indicate a first pressure state, such as a non-operational state. In other implementations, the deformation cavity 350A is sealed with a threshold amount of fluid such that the deformation cavity 350A has a set or predetermined pressure, which is less than an operational pressure of the tissue cavity 350B. Thus, deformable member 252 will deform (e.g., expand to reduce a size of deformation cavity 350A) when the pressure in the tissue cavity 350B exceeds the pressure in the deformation cavity 350A.

Figure 4:
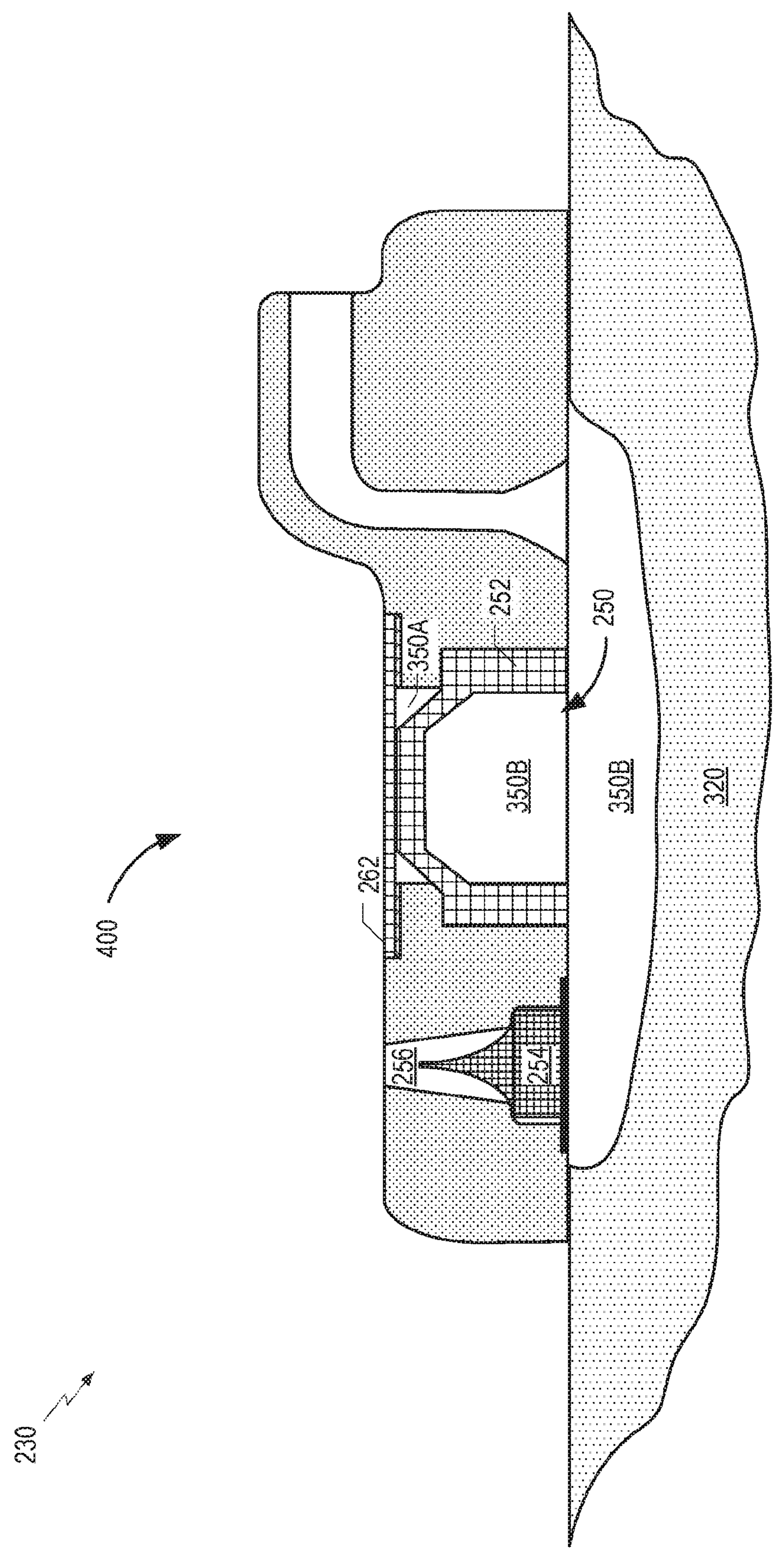
FIG. 4 is a cross-sectional view of the example of the connector of FIG. 2 in a second state.

Referring to FIG. 4, an example of connector 230 is shown in a second state 400. As shown, when connector 230 is in the second state 400, deformable member 252 is deformed (e.g., in the second state) and provides the visual indication. When the deformable member 252 is deformed (e.g., at least partially deformed) and in the second state, the visual indication provided by deformable member 252 indicates a positive-pressure state (e.g., an operational state and/or hyperbaric pressure state). When providing the visual indication, the deformable member 252 is visible or is more clearly visible (as compared to the first state 300) through the window 262. For example, at least a portion of the deformable member 252 contacts the window 262 and an outline or region of the deformable member 252 is clearly visible and/or defined. Additionally or alternatively, a color, a marking or a portion of the deformable member 252 is visible through the window 262. In FIG. 4, pressure relief valve 254 remains undeformed and is obstructing or restricting flow, as described with reference to FIG. 3. To illustrate, a force generated by the pressure differential between the tissue site 320 and ambient air does not exceed a threshold force which causes the pressure relief valve 254 to deform and enable flow.

During operation of oxygen therapy or hyperbaric therapy, positive-pressure (e.g., pressurized oxygen) is provided from an oxygen source to a portion of first channel 250 (i.e., tissue cavity 350B thereof) via a tube and conduit 272. Responsive to positive-pressure applied to first channel 250 (i.e., tissue cavity 350B thereof), deformable member 252 is configured to deform to indicate positive-pressure is being applied to tissue site 320. To illustrate, a pressure differential between the deformation cavity 350A and the tissue cavity 350B causes (e.g., forces) the deformable member 252 to deform upwards towards the window 262 and become visible to a patient or care provider via the window 262. A pressure differential between the tissue cavity 350B and ambient air does not cause the pressure relief valve 254 to deform and vent positive-pressure to ambient air via the second channel 256.

Figure 5:
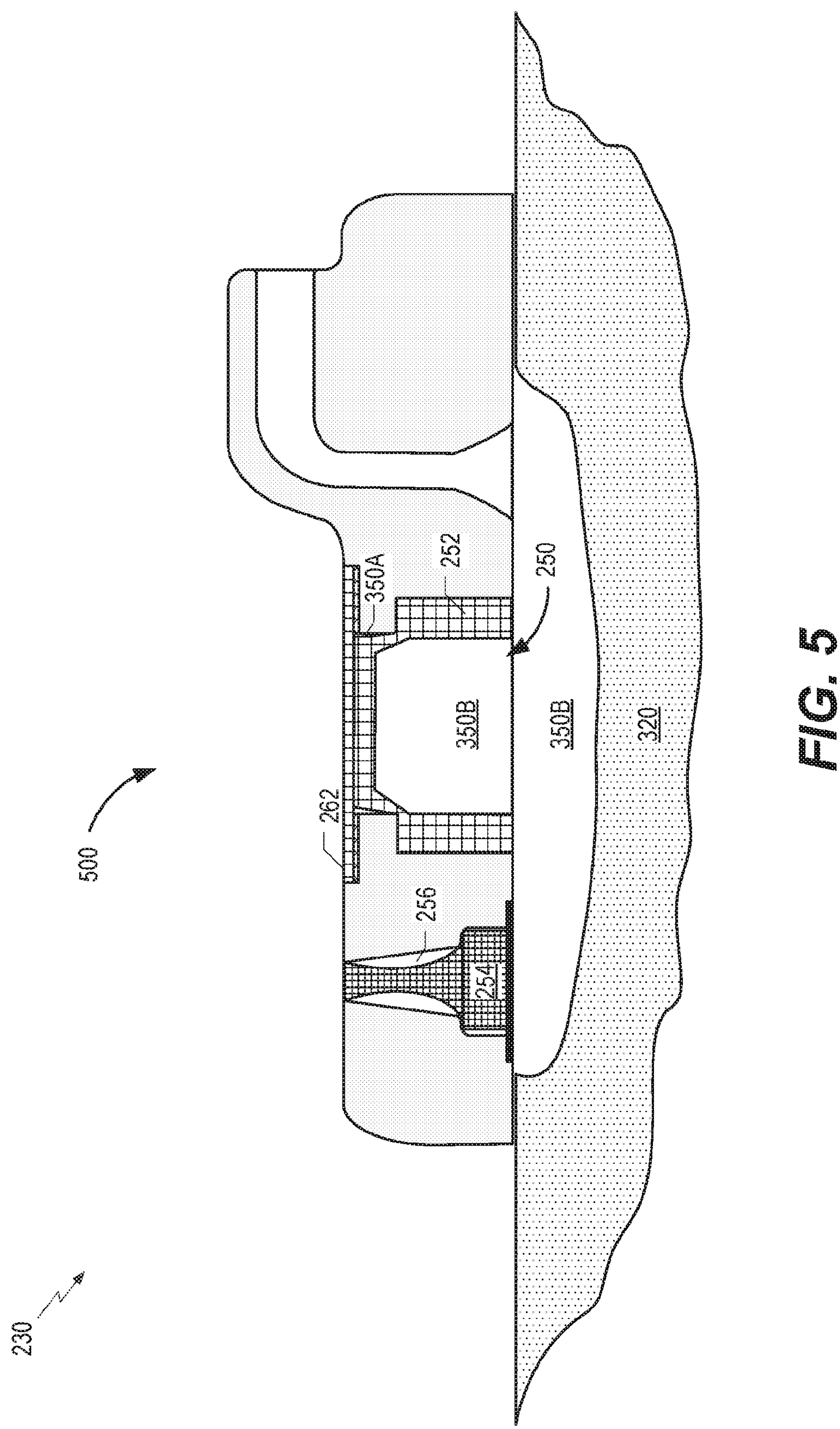
FIG. 5 is a cross-sectional view of the example of the connector of FIG. 2 in a third state.

Referring to FIG. 5, an example of a cross-section view of connector 230 is shown in a third state 500. As shown, when connector 230 is in the third state 500, the deformable member 252 is in a third state (e.g., an over deformed state or fully-deformed state). Additionally, when connector 230 is in the third state 500, the pressure relief valve 254 is configured to enable fluid (e.g., excess pressure or oxygen) to vent or evacuate from the first channel 250 via the second channel 256 (e.g., enable fluid communication between the tissue site 320 and ambient air). For example, pressure relief valve 254 is configured to, responsive to positive-pressure applied to tissue cavity 350B, deform to at least partially enable fluid communication through second channel 256 between tissue site 320 and ambient air.

During operation, the tissue cavity 350B may become exposed to excess positive-pressure, such as in the event of a regulator failure or from connection to an unregulated pressure source. When the deformable member 252 is exposed to excess positive-pressure in the tissue cavity 350B, the deformable member 252 may further deform (as compared to the second state shown in FIG. 4), such that a larger portion (as compared to the second state) of the deformable member 252 or another color or marking of the deformable member 252 is visible through the window 262, thereby indicating another pressure state. To illustrate, a greater pressure differential (as compared to the pressure differential caused by operational pressure) between the deformation cavity 350A and the tissue cavity 350B caused by excess positive-pressure forces the deformable member 252 towards the window 262 and to contact the window 262 to a greater extent than described with reference to the second state 400 of FIG. 4. For example, a first portion of deformable member 252 contacts the window 262 in the second state 400 and the first portion and a second portion of deformable member 252 contact the window 262 in the third state 500.

When the pressure relief valve 254 is exposed to excess positive-pressure in the tissue cavity 350B, a pressure differential between the tissue cavity 350B and ambient air caused by the excess positive-pressure generates a force which is greater than a threshold force which deforms the pressure relief valve 254. To illustrate, force acting upon an interior of the pressure relief valve 254 deforms the pressure relief valve 254 outwardly within second channel 256 to form an opening in the pressure relief valve 254. Accordingly, excess positive-pressure in the tissue cavity 350B is thus vented through the opening in the pressure relief valve 254 to ambient air. In other implementations, such as when the pressure relief valve 254 comprises an umbrella valve, excess positive-pressure in the tissue cavity 350B generates force on the pressure relief valve 254 to deform (e.g., collapse) the pressure relief valve 254 to form an opening or gap between the pressure relief valve 254 and the body 242. Accordingly, excess positive-pressure in the tissue cavity 350B is thus vented through the opening or gap between the pressure relief valve 254 and the body 242. Therefore, deformable member 252 and/or pressure relief valve 254 may enable effective, efficient, and safe oxygen therapy through use of the positive-pressure therapy system, thereby advancing patient reliability and confidence in the treatment.

FIGS. 6A-6E illustrate various examples of visual indications provided by the connector 230 (i.e., deformable member 252 thereof) of FIG. 2 to a patient or care provider via window 262. In FIG. 6A, deformable member 252 is configured to provide two visual indications. By providing two visual indications, deformable member 252 can indicate at least two pressure states (e.g., at least two positive-pressure states). As illustrated in FIG. 6A, deformable member 252 includes multiple colors or markings and provides a first visual indication to indicate a first pressure state when a first color or marking 602 is visible through the window 262 and provides a second visual indication to indicate a second pressure state when multiple colors or markings (e.g., both the first color or marking 602 and a second color or marking 604) are visible through the window 262. For example, deformable member 252 may deform under pressure such that the first color or marking 602 is visible to indicate a first pressure state of operational pressure and may deform to a greater extent under greater pressure such that the second color or marking 604 is visible to indicate a second pressure state of excess pressure. When the second color or marking 604 is visible, the first color or marking 602 may also be visible. Thus, a visual indication may indicate a pressure of a tissue site being greater than or equal to a pressure threshold associated with the corresponding pressure state. Additionally, deformable member 252 may provide a third indication (e.g., by not providing first and second visual indications) and indicate a third pressure state (e.g., no positive-pressure) when the deformable member 252 is not visible or is partially occluded by the window 262, such as when the deformable member 252 is in the first state and is undeformed.

In FIG. 6B, deformable member 252 is configured to provide at least three visual indications. As illustrated in FIG. 6B, the window 262 includes indicia 612, 614 as round or circular markings. Indicia 612, 614 are configured to indicate or measure a degree of deformation of deformable member 252. In the example illustrated in FIG. 6B, when the deformable member 252 is visible within first indicia 612, deformable member 252 provides a first visual indication, such as indicating a first pressure state. When the deformable member 252 is visible within an area 622 (e.g., ring) between the first indicia 612 and second indicia 614, the deformable member 252 provides a second visual indication (e.g., indicates a second pressure state), and when the deformable member 252 is visible in an area 624 outside of or past the second indicia 614, the deformable member 252 provides a third visual indication (e.g., indicates a third pressure state). For example, deformable member 252 may indicate a first pressure state of operational pressure, a second pressure state of high pressure, and a third state of excess pressure.

In FIG. 6C, deformable member 252 is configured to provide at least three visual indications indicating various pressure states. As illustrated in FIG. 6C, deformable member 252 includes multiple colors or markings 602, 604, 606, and deformable member 252 indicates a different pressure state depending on how many colors or markings 602, 604, 606 are visible or which colors or markings 602, 604, 606 are visible. Similar to FIG. 6A, each color or marking 602, 604, 606 may be associated with a different visual indication and may indicate a different pressure state when visible. For example, first color or marking 602 may be green and indicate a first pressure state, a second color or marking 604 may be yellow or orange and indicate a second pressure state, and a third color or marking 606 may be red and indicate a third pressure state.

In FIG. 6D, deformable member 252, 652 are configured to provide at least two visual indications indicating various pressure states. As illustrated in FIG. 6D, deformable members 252, 652 are arranged concentrically and each provide a visual indication which indicates a different pressure state when visible. For example, the deformable member 252 provides a first visual indication to indicate at least a first pressure state when visible and the second deformable member 652 provides a second visual to indicate at least a second pressure state when visible.

In FIG. 6E, deformable members 252, 652 are configured to provide at least three visual indications indicating various pressure states. As illustrated in FIG. 6E, deformable members 252, 652 are arranged in a side-by-side configuration. Deformable members 252, 652 function similar to the deformable members 252, 652 of FIG. 6D. Deformable members 252, 652 of FIG. 6D or 6E may have different colors or markings (e.g., colors or markings 602,604) to further provide visual indications and indicate pressure states. Although FIGS. 6A-6E are illustrated as separate configurations, aspects of each configuration can be used separately or in combination with aspects of other configurations. Additionally, although deformable members 252, 652 have circular profiles and/or indicators in FIGS. 6A-6E, in other implementations, deformable members 252, 652 have different shaped profiles and/or indicators. The visual indications and states of FIGS. 6A-6E may have pressure ranges and thresholds as described with reference to FIG. 1A. For example, a first visual indication is provided when exposed to a pressure (e.g., 15 mm Hg) within the first range of pressure and a second visual indication is provided when exposed to a second pressure within the second range of pressures (e.g., 25 mm Hg).

Referring to FIG. 7A, an illustrative example of an illustrative system 700 (e.g., a positive-pressure therapy system) is shown. System 700 includes a positive-pressure therapy device 710 (e.g., a positive-pressure therapy apparatus), a tube 714, and a dressing 716. Dressing 716 is coupled to device 710 via tube 714. Device 710 and dressing 716 may include or correspond to device 110 and dressing 116, respectively. Tube 714 may include or correspond to tube 114.

Figure 7B:
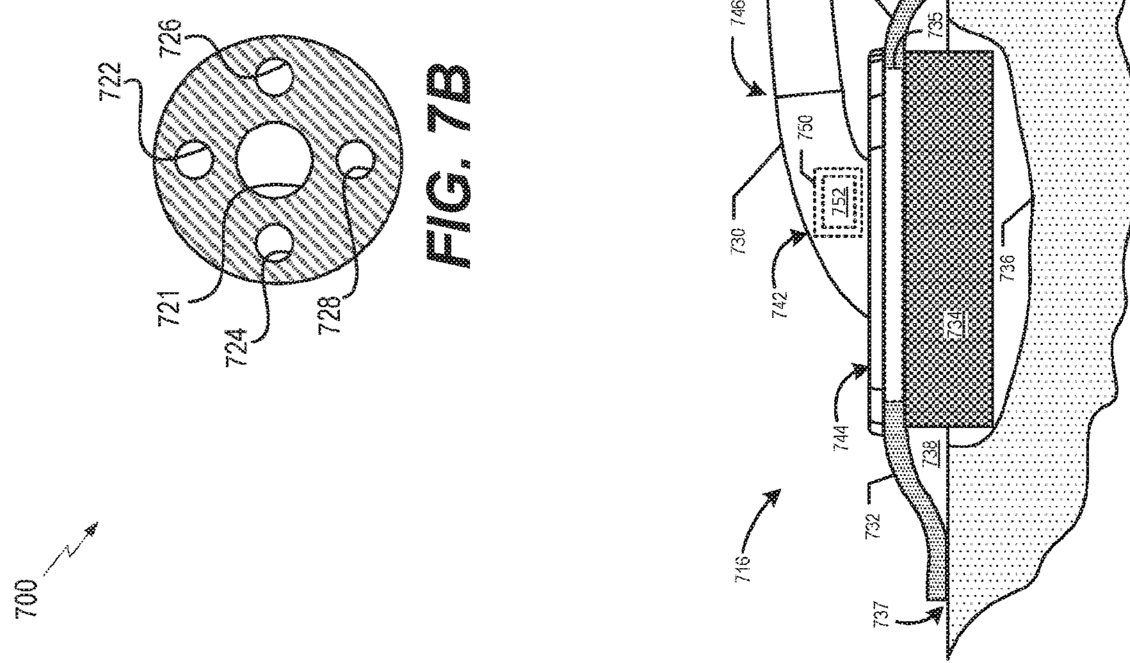

Referring to FIG. 7B, an illustrative example of a cross-section of tube 714 (when tube 114 comprises multiple lumens) along line B-B of FIG. 7A is shown. Tube 714 may include a primary lumen 721 (e.g., a positive-pressure/fluid lumen) and one or more secondary lumens, such as a first secondary lumen 722 (e.g., a negative-pressure/fluid lumen), a second secondary lumen 724 (e.g., a first sense lumen), a third secondary lumen 726 (e.g., a second sense lumen), and a fourth secondary lumen 728 (e.g., a third sense lumen). Although described as having a single primary lumen (e.g., 721), tube 714 may have multiple primary lumens, such as a first primary lumen for positive pressure and a second primary lumen for negative-pressure. Additionally, or alternatively, primary lumen 721 may be configured to for both positive-pressure and negative-pressure. Although described as having four secondary lumens, in other implementations, tube 714 may include fewer than or more than four secondary lumens. Although tube 714 has been described and/or shown as having a circular cross-sectional shape, in other implementations, tube 714 may have a cross-sectional shape other than a circle, such as an oval, triangle, quadrilateral, pentagon, star, or another shape, as illustrative, non-limiting examples. In an alternative implementation, primary lumen 721 may be a negative-pressure/fluid lumen, first secondary lumen 722 may be a positive-pressure/fluid lumen), a secondary lumens 724, 726, 728 may be sense lumens.

Dressing 716 is configured to be coupled to (e.g., adhered to) a tissue site 720 of a patient. Tissue site 720 may include or correspond to tissue site 120 or tissue site 320. Dressing 716 may include one or more components, such as a connector 730, a drape 732, a manifold 734, or a combination thereof, as illustrative, non-limiting examples. Connector 730 may include or corresponds to connector 130 or connector 230. Drape 732 and manifold 734 may include or correspond to drape 132 and manifold 134, respectively. Drape 732 may be coupled to connector 730 and/or manifold 734, and may include an opening 735 (e.g., a drape aperture) to enable communication (e.g., fluid communication) between connector 730 and manifold 734.

As shown, drape 732 is coupled to tissue site 720 via a representative adhesive 737, such as a medically acceptable, pressure-sensitive adhesive that extends about a periphery, a portion, or an entirety of drape 132. Additionally, or alternatively, drape 732 may be coupled to tissue site 720 via a double-sided drape tape, paste, hydrocolloid, hydrogel, and/or other sealing device or element, as illustrative, non-limiting examples. Drape 732 is configured to be coupled to tissue site 720 such that drape 732 covers manifold 734 (and target tissue 736) to form and/or define an interior volume 738 between drape 732 and tissue site 720 (e.g., target tissue 736). To illustrate, interior volume 738 may correspond to a sealed therapeutic environment. For example, the tissue proximate the target tissue 736 may be undamaged epidermis peripheral to target tissue 736. The sealed therapeutic environment may be isolated from an external environment, such as an external environment at ambient pressure. Interior volume 738 may include or correspond to tissue cavity 350B.

As shown, manifold 734 is positioned within interior volume 738 at (e.g., on or above) target tissue 736 of tissue site 720. In some implementations, manifold 734 may contact tissue site 720, target tissue 736, or both. In some implementations, such as when target tissue 736 extends into tissue from a tissue surface 719 creating a cavity (e.g., 350B), manifold 734 may partially or completely fill the cavity. In other implementations, manifold 734 may be placed over target tissue 736. Manifold 734 may take one or more forms, and/or may have one or more configurations (e.g., sizes, shapes, and/or thicknesses), depending on one or more factors, such as the type of treatment being implemented, the nature and size of target tissue 736, a stage of treatment, or a combination thereof. For example, the size and shape of the manifold 734 may be adapted to target tissue 736 and/or tissue site 720. To illustrate, manifold 734 may be adapted to a contours of target tissue 736 and/or tissue site 720. In a particular implementation, manifold 734 includes a foam, such as GranuFoam® material manufactured by Kinetic Concepts, Incorporated of San Antonio, Tex., as an illustrative, non-limiting example.

Connector 730 may include a connector body 742, a base 744, and an interface 746 (e.g., a port). Connector body 742 (e.g., a housing) may include or correspond to body 142 or body 242. Base 744 may include or correspond to base 144 or base 244. Interface 746 may include or correspond to interface 146 or interface 246. Interface 746 is configured to be coupled to tube 714.

Body 742 may define one or more cavities, such as a channel 750 (e.g., a first channel) into which a deformable member 752 is positioned. Channel 750 may include or correspond to channel 150 or first channel 250, and channel 750 may include deformation cavity 350A and/or a portion of tissue cavity 350B or interior volume 738. The deformable member 752 may include or correspond to deformable member 152, deformable member 252, or deformable member 652. As described further herein, deformable member 752 is configured to at least partially deform responsive to positive-pressure applied to a portion of channel 750, i.e., tissue cavity 350B thereof. Additionally, a second deformable member (e.g., deformable member 652) may be positioned in the first channel 750.

Additionally, body 742 may include one or more channels, such as one or more channels in fluid connection with first channel 750. For example, body 742 may include a second channel, into which a pressure relief valve is positioned, that is in fluid communication with first channel 750 via tissue site 720. The second channel may include or correspond to second channel 256, and the pressure relief valve may include or correspond to pressure relieve valve 154 or pressure relieve valve 254. Additionally or alternatively, body 742 may include a third channel into which a second deformable member (e.g., deformable member 652) is positioned.

Further, body 742 may include one or channels or conduits, that extend from and/or are coupled to interface 146. For example, body 742 may include a conduit and a secondary channel (e.g., a reduced-pressure or exudate channel) that are in fluid communication with interior volume 738. To illustrate, the secondary channel may have an aperture defined by base 744, and which is positioned over manifold 734, to enable fluids and/or exudate to be drawn from target tissue 736. In some implementations, connector 730 may be positioned on manifold 734 such that a perimeter of the aperture (defined by base 744) is in direct contact with manifold 734. When the conduit (e.g., 272) and the second channel (e.g., 254) are in fluid communication with interior volume 738, connector 730 may operate to maintain fluid communication between interior volume 738 and device 710 via tube 714, and to prevent fluid communication between interior volume (e.g., a sealed therapeutic environment formed by dressing 716) and the ambient environment.

Referring to channel 750 and deformable member 752, deformable member 752 is configured to provide at least one visual indication responsive to pressure at tissue site 720 and/or interior volume 738. For example, deformable member 752 may be transitionable between a first state (e.g., an undeformed state) in a second state (e.g., a deformed state). In the first state (e.g., the undeformed state), deformable member 752 is configured and/or positioned to indicate a first pressure state, such as a neutral pressure state (e.g., a barometric pressure state) by not providing the visual indication. When deformable member 752 is in the second state, deformable member 752 is configured to provide the visual indication to indicate a second pressure state, such as a hyperbaric pressure state (e.g., a positive-pressure state) or an operational pressure state. For example, deformable member 752 may transition (e.g., deform) from the first state to the second state responsive to positive-pressure applied to the tissue cavity (e.g., 350B) of channel 750, thereby being visible through a viewing member (e.g., 162) or window (e.g., 262) of the connector 730 or increasing visibility of the deformable member 752 through the window.

Referring to channel 750 and the pressure relief valve, the pressure relief valve is configurable to enable or create a flow path through the second channel responsive to pressure. For example, deformable member 752 may transition (e.g., deform by constricting or expanding) from obstructing or restricting flow to enabling flowing through the second channel (e.g., 256) to vent pressure from tissue site 720 by generating an opening within the second channel.

Tube 714 includes one or more lumens. For example, tube 714 may include a positive-pressure/fluid lumen (e.g., 121), a negative-pressure/fluid lumen, and one or more sense lumens. As shown, a first end of tube 714 is coupled to dressing 716 and a second end of tube 714 is coupled to device 710. In some implementations, the second end of tube 714 may include a therapy device connector configured to couple (e.g., mate) with device 710.

Device 710 includes a controller 760, one or more interfaces 762, one or more I/O devices 764, and one or more connectors, such as a representative connector 766. Device 710 further includes one or more conduits 768, a fluid chamber 770, pressure sensors 772, 774, one or more valves 776 (e.g., solenoid valves), and a positive-pressure source 778.

Connector 766, such as connector 138, is configured to be coupled to tube 714, such as the second end of tube 714. Connector 766 includes one or more port/interfaces, such as a first port/interface 780, a second port/interface 782, a third port/interface 784, a fourth port/interface 786. When connector 766 is coupled to tube 714, the positive-pressure/fluid lumen (e.g., 721) is in fluid communication with first port/interface 780, the negative-pressure/fluid lumen (e.g., 722) is in fluid communication with second port/interface 782, first sense lumen (e.g., 724) is in fluid communication with third port/interface 784, and second sense lumen (e.g., 726) is in fluid communication with fourth port/interface 786.

Each of first port/interface 782, second port/interface 782, third port/interface 784, and fourth port/interface 786 is coupled to one or more components of device 710 via one or more conduits (e.g., 768). For example, first port/interface 780 is coupled to positive-pressure source 778, second port/interface 782 is coupled through fluid chamber 770 (e.g., a canister or a liquid-collection cavity) to negative-pressure source 779, third port/interface 784 is coupled to a first pressure sensor 772, and fourth port/interface 786 is coupled to a second pressure sensor 774. The sensors 772, 774 may be configured to generate data indicative of pressure within dressing 716. Although described as having two pressure sensors (e.g., 772, 774), in other implementations, device 710 may include fewer than two pressure sensors, such as no pressure sensors or a single pressure sensor, or more than two pressure sensors. Additionally, each of first port/interface 780, second port/interface 782, third port/interface 784, and fourth port/interface 786 is coupled to a corresponding valve (e.g., 776), such as a solenoid valve, which is configured to change pressure from dressing 716. First port/interface 780 is coupled to positive-pressure source 778 and a corresponding valve 776 via a conduit 768.

Positive-pressure source 778 is configured to provide positive-pressure to interior volume 738 of dressing 716 such that interior volume 738 is expanded, and/or positive-pressure is applied to at least target tissue 736. Positive-pressure source 778 may include a mechanically and/or electrically-powered device, such as a manually-actuated or manually-charged pump, an oxygen tank, an oxygen collector, a wall port, a micro-pump, a disc-pump, and/or the like, as illustrative, non-limiting examples.

In some implementations, device 710 further includes reduced-pressure source 779 that is configured to provide negative-pressure to interior volume 738 of dressing 716 such that interior volume 738 is reduced, and/or negative-pressure is applied to at least target tissue 736. Reduced-pressure source 779 may include a mechanically and/or electrically-powered device, such as a manually-actuated or manually-charged pump, a vacuum pump, an electrically-driven vacuum pump, a suction pump, a wall suction port, a micro-pump, a disc-pump, and/or the like, as illustrative, non-limiting examples. As illustrated in FIG. 7A, the positive-pressure source 778 and the reduced-pressure source 779 may operate in conjunction with each other and are applied to different portions of tissue site 720 via different lumens (e.g., 721, 722) of tube 714. In other implementations, the positive-pressure source 778 and the reduced-pressure source 779 share a lumen (e.g., 721 or 722) of tube 714 and the reduced-pressure source 779 operates in the alternative to the positive-pressure source 778 (e.g., operate in distinct cycles). For example, the reduced-pressure source 779 operates before or after the positive-pressure source 778 to remove exudate from tissue site 720.

Controller 760 includes a processor 790 coupled to a memory 792 (e.g., a computer-readable storage device). Memory 792, such as a non-transitory computer-readable storage medium, may include volatile memory devices (e.g., random access memory (RAM) devices), nonvolatile memory devices (e.g., read-only memory (ROM) devices, programmable read-only memory, and flash memory), or both. Memory 792 may be configured to store instructions 794, a pressure profile 796, and one or more thresholds 798. Instructions 794 may be configured to, when executed by the one or more processors 790, cause the processor(s) 790 to perform one or more operations.

Pressure profile 796 may include desired target pressures to be provided to a patient over a time period. In some implementations, the pressure profile 796 may include a set-up profile applying target pressures at the commencement of therapy treatments and a maintenance profile for applying target pressure during therapy. One or more thresholds 798 may include one or more one or more pressure thresholds, one or more time thresholds, one or more other thresholds, or a combination thereof.

Processor 790 may include a microcontroller/microprocessor, a central processing unit (CPU), a field-programmable gate array (FPGA) device, an application-specific integrated circuits (ASIC), another hardware device, a firmware device, or any combination thereof. Processor 790 may be configured to execute instructions 794, execute and/or operate according to pressure profile 796, and/process sensor data generate by sensors 772, 774. For example, processor 790 may be configured to process sensor data (e.g., pressure signals) received by one or more sensors (e.g., 772, 774) and/or monitor the sensor data. Additionally, or alternatively, processor 790 may be configured to issue one or more alerts according to a pre-determined pressure therapy (e.g., pressure profile 796) for a patient and/or based on one or more thresholds 798. In some implementations, the one or more alerts may be in the form of a visual alert (e.g., a light indicator), a tactile alert, an audible alert, a message presented via a display, or a message transmitted to another device. In the event that processor 790 determines that pressure profile 796 is being implemented, processor 790 may provide an indication that the sensor data (e.g., the monitored pressure at dressing 716) is following pressure profile 796. For example, processor 790 may initiate a visual indication (e.g., a light indicator), a tactile indication, an audible indication, a message presented via a display, or a message transmitted to another device.

The one or more interfaces 762 may include a wired interface, a wireless interface, or both. In some implementation, the one or more interfaces 762 may include a network interface and/or a device interface configured to be communicatively coupled to one or more other devices. For example, interfaces 762 may include a transmitter, a receiver, or a combination thereof (e.g., a transceiver), and may enable wired communication, wireless communication, or a combination thereof. Additionally, or alternatively, the one or more interfaces 762 may include serial interfaces (e.g., universal serial bus (USB) interfaces or Institute of Electrical and Electronics Engineers (IEEE) 1394 interfaces), parallel interfaces, display adapters, audio adapters, and other interfaces. The one or more I/O devices 764 may include a mouse, a keyboard, pointing devices, a display device, the camera, speakers, microphones, touch screens, other I/O devices, or a combination thereof. Processor 790 may configured to send and/or receive data via the interface (s) 762 and/or the I/O device(s) 764.

During operation, dressing 716 is coupled to tissue site 720 so as to cover target tissue 736. Additionally, dressing 716 is coupled to device 710 via tube 714. In some implementations, processor 790 receives an input via I/O device 764, such as a touchscreen, to select a pressure profile (e.g., 796) of multiple pressure profiles stored at memory 792, to initiate positive-pressure therapy, or both. Alternatively, the input may indicate a value of a positive-pressure to be provided and/or maintained. Responsive to the input, controller 760 (e.g., processor 790) generates one or more commands to initiate operations of one or more components of device 710. For example, processor 790 may access pressure profile 796 (e.g., a set-up profile or a maintenance profile). Additionally, or alternatively, processor 790 may activate and/or regulate positive-pressure source 778, one or more valves 776, or both. In some implementations, processor 790 may control operation of positive-pressure source 778, one or more valves 776 based on at least in part on the input (e.g., the pressure profile 796 selection or the value of the positive-pressure).

Responsive to one or more signals (e.g., commands) from processor 790, positive-pressure source 778 may apply positive-pressure to dressing 716. For example, positive-pressure developed by positive-pressure source 778 may be delivered through tube 714 to connector 730 of dressing 716. Accordingly, the positive-pressure source 778 can increase a pressure in interior volume 738. Internal volume (e.g., a sealed therapeutic environment) and/or target tissue 736 may be isolated from an external environment (associated with an ambient pressure).

As positive-pressure is provided via pressure/fluid lumen (e.g., 121), pressure at dressing 716 may be communicated to first pressure sensor 772 and second pressure sensor 774 via first sense lumen (e.g., 724) and second sense lumen (e.g., 726), respectively. The pressure communicated by via first sense lumen (e.g., 724) and second sense lumen (e.g., 726) may be representative of the pressure at the target tissue 736. Each of first pressure sensor 772 and second pressure sensor 774 are configured to generate sensor data that is communicated to controller 760 (e.g., processor 790). The sensor data provided to controller 760 enables device 710 to track treatment provided to target tissue 736 via dressing 716. Based on the sensor data, controller 760 (e.g., processor 790) may initiate operation of one or more valves (e.g., 776) between an open position and a closed position. For example, processor 790 may be configured to adjust a particular valve in response to a comparison of the sensor data (indicating that a pressure within the interior volume (e.g., 738) to a threshold (e.g., 798).

In some implementations, processor 790 is configured to control positive-pressure source 778 (e.g., a positive-pressure source device) and/or one or more valves 776 based at least in part on the sensor data. For example, processor 790 may be configured to deactivate positive-pressure source 778 in response to a determination that the sensor data indicates that a pressure within the interior volume (e.g., 738) is less than a first threshold (e.g., a first threshold pressure value). In some implementations, processor 790 is configured to operate at least one valve (e.g., 776) towards the open position upon or after deactivation of positive-pressure source 778. To illustrate, the at least one valve may include the valve coupled to positive-pressure source 778, the valve coupled to first pressure sensor 772, and/or the valve coupled to second pressure sensor 774. As another example, processor 790 may be configured to activate positive-pressure source 778 in response to a determination that the sensor data indicate that a pressure within the interior volume (e.g., 738) is greater than or equal to a second threshold (e.g., a second threshold pressure value). Activation of positive-pressure source 778 may increase pressure within the interior volume (e.g., 738). In some implementations, processor 790 is configured to operate at least one valve (e.g., 776) towards the closed position upon or after activation of positive-pressure source 778. The first threshold and the second threshold may have the same value. Alternatively, the first threshold and the second threshold may have different values (e.g., the second threshold may be greater than the first threshold).

In some implementations, valve 776 coupled to first pressure sensor 772 may be operated independent of valve 776 coupled to second pressure sensor 774. For example, controller 760 may operate valve 776 coupled to first pressure sensor 772 based on sensor data received from first pressure sensor 772 and/or based on a first set of one or more thresholds (e.g., 798). Controller 760 may operate valve 776 coupled to second pressure sensor 774 based on sensor data received from second pressure sensor 774 and/or based on a second set of one or more thresholds (e.g., 798). The first set of one or more thresholds and the second set of one or more thresholds may include one or more of the same threshold value(s) and/or one or more different threshold value(s). Additionally, or alternatively, in other implementations, controller 760 may operate one or more of the valves based on an average of sensor data of two or more sensors. For example, controller 760 may control one or more valves, such as the valve coupled to positive-pressure source 778 based on an average of the sensor data (received from sensors 772, 774) and a third set of one or more thresholds. The third set of one or more thresholds may include one or more of the same threshold value(s) and/or one or more different threshold value(s) as the first set of one or more thresholds and/or the second set of one or more thresholds.

Positive-pressure provided by positive-pressure source 778 via tube 714 can cause pressurized fluid (e.g., oxygen) to be provided to target tissue 736 (e.g., tissue site 720) via tube 714 (e.g., positive-pressure/fluid lumen) and first port/interface 780. In some implementations, device 710 may include a sensor and/or regulator (not shown) coupled to controller 760 (e.g. processor 790) and configured to monitor a pressure of the positive-pressure source 778 or the corresponding conduit 768 thereof. For example, processor 790 may receive sensor data from the sensor that indicates a pressure level of the regulator and may operate valve 776 to control a pressure and/or volume of positive-pressure source 778. Once a desired pressure of fluid is achieved, the pressurized fluid (e.g., oxygen) may be provided to target tissue 736.

Reduced-pressure provided by reduced-pressure source 779 via tube 714 can cause exudate, fluid, and/or another material to be drawn (e.g., removed) from target tissue 736 (e.g., tissue site 720) via tube 714 (e.g., reduced-pressure/fluid lumen) and second port/interface 782. Exudate, fluid, and/or another material removed via second port/interface 782 may be collected in fluid chamber 770 (e.g., a canister) for disposal. In some implementations, device 710 may include a sensor (not shown) coupled to controller 760 (e.g. processor 790) and configured to monitor a volume of fluid chamber 770. For example, processor 790 may receive sensor data from the sensor that indicates a fill level of fluid chamber 770. In response to a determination by processor 790 that the fill level is greater than or equal to a threshold (e.g., a threshold fill level value), processor 790 is configured to deactivation of reduced-pressure source 779, operate at least one valve (e.g., 776) towards the open position, or both. Additionally, or alternatively, based on a determination by processor 790 that the fill level is greater than or equal to a threshold, processor 790 may initiate a notification (e.g., an alarm), such as a message via a display, an audio and/or visual notification, transmit a data message to another device, or a combination thereof.

If device 710 is coupled to dressing 716 such that positive-pressure is provided to tissue site 720 and/or interior volume 738, deformation of deformable member 752 occurs and deformable member 752 provides a visual indication. When deformable member 752 provides the visual indication, deformable member 752 may be in a deformed state (e.g., the second state), and deformable member 752 may indicate a positive-pressure state (e.g., a hyperbaric state) via the window, i.e., that oxygen therapy is being applied to the tissue site 720. By deformable member 752 indicating a positive-pressure state or operational status, electronic monitoring and regulation of an oxygen source or a positive-pressure level at the dressing 716, at the therapy device 710, or both, can be eliminated.

Thus, FIG. 7A describes system 700 for providing positive-pressure therapy. System 700 may advantageously include connector 730 (e.g., channel 750 and deformable member 752) configured to indicate a pressure state of connector 730, channel 750, tissue site 720, or a combination thereof. For example, if positive-pressure is not applied to channel 750, deformable member 752 does not deform (e.g., expand) to create an indication visible by a patient or care provider through the window. If positive-pressure is applied to channel 750, deformable member 752 may deform (e.g., expand) to create an indication visible by a patient or care provider through the window. Additionally, the deformable member 752 or a second deformable member 752 (e.g., the second deformable member 652) may be configured to deform to indicate an over-pressurized state, as described with reference to FIGS. 1 and 6A-6E. Thus, an operational status of oxygen therapy can be obtained without using electronics and by the use of flexible and compliant materials.

Additionally, System 700 may advantageously include pressure relief valve to enable or generate a flow path to reduce or limit an amount of positive-pressure at the tissue site 720 if positive-pressure is provided to channel 750. To illustrate, if positive-pressure is applied to channel 750, pressure relief valve may expand (e.g., deform) to create an aperture from the channel 750 to ambient air, thereby avoiding or limiting excess positive-pressure and/or capillary collapse at tissue site 720. Accordingly, deformable member 752 and/or pressure relief valve may enable effective, efficient, and safe positive-pressure therapy through use of system 700, thereby advancing patient reliability and confidence in the treatment. Furthermore, system 700 may be configured to include a reduced-pressure therapy system and the hyperbaric oxygen therapy can be applied concurrently with reduced-pressure therapy or separately from reduced-pressure therapy to obtain the benefits of positive and negative-pressure therapy.

Figure 8:
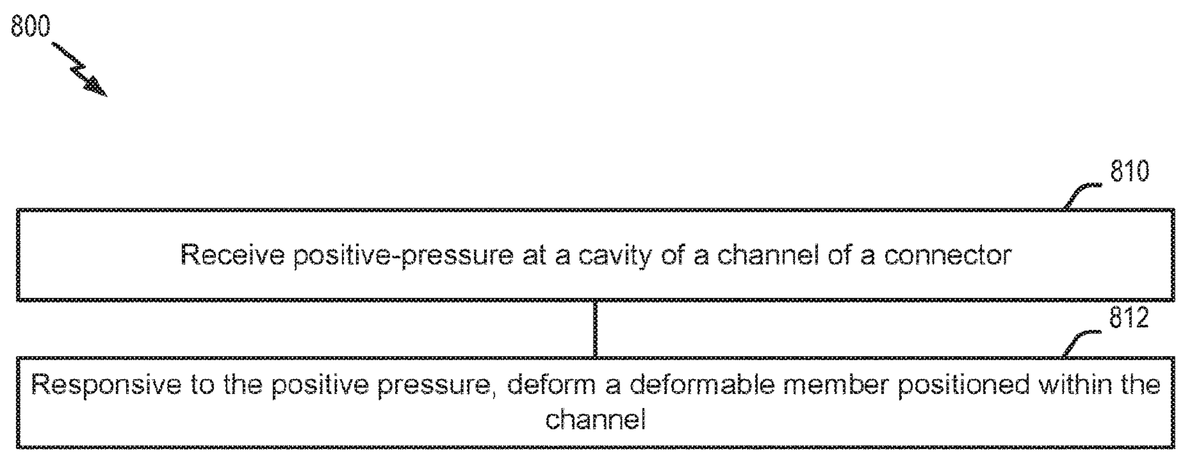
FIG. 8 is a flowchart illustrating an example of a method of operation of a connector.

FIG. 8 illustrates a method 800 of operating a connector (of a dressing). The method 800 may be performed at or by a connector, such as connector 130, connector 230, or connector 730. In some implementations, the connector may be included in a positive-pressure system (e.g., a hyperbaric oxygen therapy system), such as system 100 (e.g., connector 130), a system that includes connector 230, or the system 700 (e.g., connector 730).

Method 800 includes receiving positive-pressure at a cavity of a channel of a connector, at 810. The channel may include or correspond to channel 150, first channel 250, or channel 750, and the cavity may include or correspond to tissue cavity 350B or interior volume 738. The positive-pressure (e.g., pressurized oxygen) may be received at the connector from the positive-pressure source via a tube, such as tube 114 or tube 714.

Method 800 further includes, responsive to the positive pressure, deforming a deformable member positioned within the channel of the connector, at 812. For example, the deformable member may include or correspond to deformable member 152, deformable member 252, deformable member 652, or deformable member 752.

Thus, method 800 describes operation of a connector to mechanically indicate a pressure state and/or an amount of pressure at the tissue site. Therefore, a patient or care provider can easily determine if the tissue site is receiving positive-pressure without the use of electronics, and if desired adjust the positive-pressure. Accordingly, the connector may enable effective, efficient, and safe reduced-pressure therapy through use of the reduced-therapy system.

Figure 9:
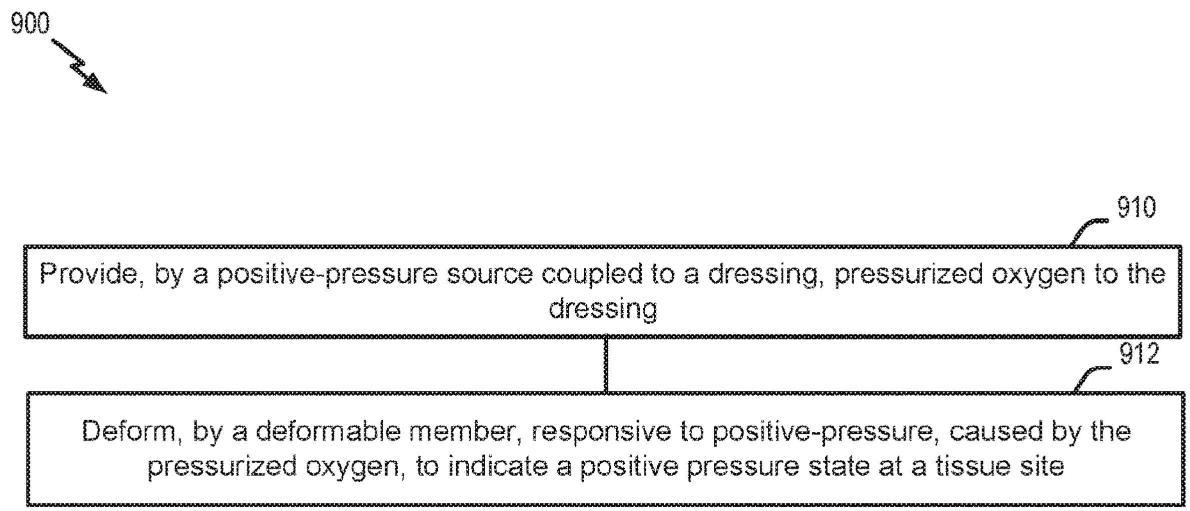
FIG. 9 is a flowchart illustrating an example of a method of operation of positive-pressure system.

FIG. 9 illustrates a method 900 of operating a positive-pressure system. The method 900 may be performed at or by system 100 (e.g., dressing 116), a system that includes connector 230, or the system 700 (e.g., dressing 716).

Method 900 includes providing, by a positive-pressure source coupled to a dressing, pressurized oxygen to the dressing, at 910. For example, the positive-pressure source may include or correspond to positive-pressure source 178 or positive-pressure source 778. The dressing may include or correspond to dressing 116, a dressing that includes connector 230, a dressing that includes dressing 716. To illustrate, oxygen is provided by the positive-pressure source via tube 114 or tube 714 to the dressing, such as to a connector thereof. The connector may include or correspond to connector 130, connector 230, or connector 730.

Method 900 further includes deforming, by a deformable member of the dressing, responsive to positive-pressure, caused by the pressurized oxygen, to indicate a positive pressure state at a tissue site, at 912. For example, the deformable member may include or correspond to deformable member 152, deformable member 252, deformable member 652, or deformable member 752. The tissue site may include or correspond to tissue site 120, tissue site 320, tissue site 720, and/or target tissue 736. The positive pressure state may include or correspond to a hyperbaric state and thus, the dressing mechanically indicates a pressure state and/or an amount of pressure at the tissue site. To illustrate, deformable member deforms to provide a visual indication that indicates a pressure or operational state. Therefore, a patient or care provider can easily determine if the dressing and/or the tissue site is receiving positive-pressure without the use of electronics. Thus, method 900 describes operation of a positive-pressure system (e.g., a hyperbaric oxygen therapy system), and the positive-pressure system may be configured to ensure effective, efficient, and safe reduced-pressure therapy.

It is noted that one or more operations described with reference to one of the methods of FIGS. 8-9 may be combined with one or more operations of another of FIGS. 8-9. For example, one or more operations of method 800 may be combined with one or more operations of method 900. Additionally, or alternatively, one or more operations described above with reference to FIGS. 1A, 1B, 2-5, 6A-6E, 7A, and 7B may be combine with one or more operations of FIG. 8, FIG. 9, or a combination of FIGS. 8 and 9.

The above specification and examples provide a complete description of the structure and use of illustrative examples. Although certain aspects have been described above with a certain degree of particularity, or with reference to one or more individual examples, those skilled in the art could make numerous alterations to aspects of the present disclosure without departing from the scope of the present disclosure. As such, the various illustrative examples of the methods and systems are not intended to be limited to the particular forms disclosed. Rather, they include all modifications and alternatives falling within the scope of the claims, and implementations other than the ones shown may include some or all of the features of the depicted examples. For example, elements may be omitted or combined as a unitary structure, connections may be substituted, or both. Further, where appropriate, aspects of any of the examples described above may be combined with aspects of any of the other examples described to form further examples having comparable or different properties and/or functions, and addressing the same or different problems. Similarly, it will be understood that the benefits and advantages described above may relate to one example or may relate to several examples. Accordingly, no single implementation described herein should be construed as limiting and implementations of the disclosure may be suitably combined without departing from the teachings of the disclosure.

The previous description of the disclosed implementations is provided to enable a person skilled in the art to make or use the disclosed implementations. Various modifications to these implementations will be readily apparent to those skilled in the art, and the principles defined herein may be applied to other implementations without departing from the scope of the disclosure. Thus, the present disclosure is not intended to be limited to the implementations shown herein but is to be accorded the widest scope possible consistent with the principles and novel features as defined by the following claims. The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A connector for a dressing, the connector comprising:

a connector body configured to define at least a portion of a first channel;

a viewing member coupled to the connector body; and a deformable member positioned within the first channel and configured to deform based on a pressure of a cavity partially defined by the deformable member and to provide a visual indication, via the viewing member, of the pressure of the cavity, the cavity being distinct from a second cavity defined by the connector body, the viewing member, and the deformable member;

the deformable member being further configured to:

provide a first visual indication, via the viewing member, if the pressure of the cavity is greater than or equal to a first threshold; and deform responsive to a force resulting from a pressure differential between the cavity and the second cavity.

2. The connector of claim 1, wherein the deformable member comprises an elastic polymer.

3. The connector of claim 2, wherein:

the deformable member is configured to deform to transition between a first state and a second state, when the deformable member is in the first state, the deformable member is configured to indicate a neutral pressure state, and when the deformable member is in the second state, at least a portion of the deformable member is viewable through the viewing member and configured to indicate a positive-pressure state.

4. The connector of claim 3, wherein the first state comprises an undeformed state, and wherein the second state comprises a deformed state.

5. The connector of claim 4, wherein:

when the deformable member is in the first state, the deformable member does not contact the viewing member, and when the deformable member is in the second state, at least a first portion of the deformable member contacts the viewing member.

6. The connector of claim 5, wherein the first portion has a first color or marking.

7. The connector of claim 6, wherein:

the deformable member is configured to provide a second visual indication, via the viewing member, when the pressure of the cavity is greater than or equal to a second threshold.

8. The connector of claim 7, wherein:

the deformable member is configured to deform to transition between the second state and a third state, when the deformable member is in the third state, at least a second portion of the deformable member contacts the viewing member, the second portion has a second color or marking that is different from the first color or marking of the first portion, and the first state corresponds to a first range of pressures, the second state corresponds to a second range of pressures, and the third state corresponds to a third range of pressures.

9. The connector of claim 8, wherein the second visual indication indicates an over-pressure state.

10. The connector of claim 9, wherein the deformable member is configured to transition to the second state between 10 mm Hg and 22 mm Hg.

11. The connector of claim 10, wherein the deformable member has a hardness in the range of 10 Shore A to 20 Shore A.

12. The connector of claim 11, further comprising a pressure relief valve positioned within a second channel defined by the connector body and configured to enable flow when the pressure of the cavity is greater than equal to a threshold value.

13. The connector of claim 12, wherein:

the pressure relief valve includes a valve selected from the group consisting of: a duckbill valve, an umbrella valve, and a combination duckbill umbrella valve, and optionally, the pressure relief valve has a hardness in the range of 40 Shore A to 60 Shore A.

14. The connector of claim 13, wherein the pressure relief valve is configured to generate an audio indication responsive to flow through the pressure relief valve.

15. The connector of claim 14, wherein the threshold value associated with the pressure relief valve is between 22 mm Hg and 35 mm Hg.

16. The connector of claim 15, wherein the viewing member comprises a window.

17. The connector of claim 16, wherein the window comprises a transparent material or a translucent material such that the deformable member is at least partially occluded by the window in when the deformable member is in the first state and is visible via the window when the deformable member is in a second state.

18. The connector of claim 17, wherein the window comprises frosted glass and is semi-opaque.

* * * * *